United States Patent [19]

Nair et al.

[11] Patent Number: 4,871,736
[45] Date of Patent: Oct. 3, 1989

[54] STEREOISOMERIC TRICYCLIC BIS(DIOXOPIPERAZINES) AND PHARMACEUTICAL COMPOSITIONS

[75] Inventors: Raghunathan V. Nair, Columbus; Donald T. Witiak, Mt. Vernon, both of Ohio

[73] Assignee: The Ohio State University, Columbus, Ohio

[21] Appl. No.: 934,757

[22] Filed: Nov. 25, 1986

[51] Int. Cl.$^4$ .................. A61K 31/535; C07D 413/14
[52] U.S. Cl. .................... 514/232.5; 544/81; 544/229; 544/346; 544/406; 544/408
[58] Field of Search ........................ 544/81; 514/232.5

[56] References Cited

PUBLICATIONS

Witiak et al., 28 *J. Med. Chem.*, 1228 (1985).

*Primary Examiner*—Robert W. Ramsuer
*Attorney, Agent, or Firm*—Emch, Schaffer, Schaub & Porcello Co.

[57] ABSTRACT

Stereoisomeric tricyclic bis(dioxopiperazines) of the formula

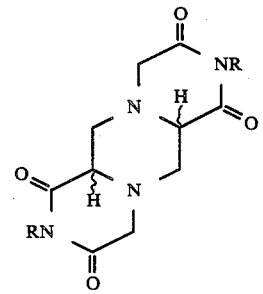

wherein R is H or

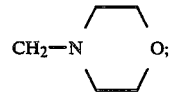

and the processes for the synthesis thereof are provided. The compounds are effective as antitumor or antimetastatic drugs.

3 Claims, 7 Drawing Sheets

STEREOISOMERIC TRICYCLIC BIS(DIOXOPIPERAZINES) AND PHARMACEUTICAL COMPOSITIONS

BACKGROUND OF THE INVENTION

This application is a continuation-in-part of Ser. No. 596,364; filed Apr. 3, 1984, now abandoned.

Cancer remains a major cause of death in technologically advanced societies, leading to many scientific efforts to determine its origin and, thereby, effect cures. Although several theories for carcinogenesis have been explained, the origin of most cancers remain a mystery, although they are known to be related to varius environmental factors. Unlike normal cells, cancerous cells do not exhibit the properties of cellular differentiation, organ size limitation or hormonal regulation. Lacking these limiting properties, such malignant cells will invade surrounding tissues and under metastasis to form secondary tumors in other organs. Cancer metastasis is a major obstacle in achieving a cure for this disease and the prevention of such multiple secondary tumor growth remains an important goal.

The effectiveness of an anticancer drug depends upon its selectivity in destroying the cancerous cells without damaging other critical tissue. Surgery, radiotherapy and chemotherapy have been used alone or in combination as an effective treatment for cancer. While surgery and radiotherapy can eradicate a localized tumor, it is not useful in curing a metastatic disease. Chemotherapy can be useful in the treatment of some cancer metastasis.

Cancer chemotherapeutic agents have been generally classified into various categories such as alkylating agents, antimetabolites, antibiotics, vinca alkaloids and miscellaneous. Many of these agents kill cells by interfering with DNA synthesis or function. However, none of the clinically used chemotherapeutic agents have shown any selective antimetastatic property.

Bis(dioxopiperidines) are a unique class of antitumor agents. Based upon the observation (Furst, A. in Chemistry of Chelation in Cancer, Thomas, Ed., Springfield, IL, 1963), that some useful antitumor agents are actual or potential chelating agents, bis(dioxopiperazines) were developed as prodrugs of the chelating agents such as ethylenediaminetetraacetic acid (EDTA) (1). Among several prior art compounds synthesized by Creighton et al. a few exhibited cytotoxic effects in experimental tumor models. See, Creighton, A. M., Hellmann, K., and Whitecross, S. Nature (London) 1969, 222, 384–385; Creighton, A. M. Progr. Antimicrob. and Anticancer Chemother. 1970, 1, 167–169; Creighton, A. M. Brit. Patent 1971, 1,234,935; Creighton, A. M. Brit. Patent 1974, 1,374,979.

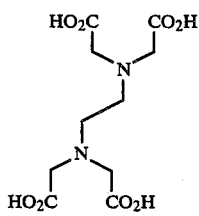

Bis(dioxopiperazine) 2 prepared from 1 was active in the leukemia L1210 and Sarcoma S180 tumor models as reported by Creighton et al., 1969, supra. The bis(dioxopiperazine) 3 (Razoxane) has been subjected to numerous clinical trials. See, Adamson, R. H. in Antineoplastic and Immunosuppressive Agents Part II. Handbook of Experimental Pharmacology, Sartorelli, A. C. and Johns. D. G., Eds., Springer-Verlag, NY 1975, XXXVIII/2, 885–886; Bakowski, M. T., Cancer Treat. Rev. 1976, 3, 95–107; Bellet, R. E., Rozencweig, M., Von Hoff, D. D., Penta, J. S., Wasserman, T. H. and Muggia, F. M., Europ. J. Cancer 1977, 13, 1293–1298; and Herman, E. H., Witiak, D. T., Hellmann, K, and Warvdekar, V. S., Adv. in Pharmacol. and Chemother. 1982, 19, 249–290.

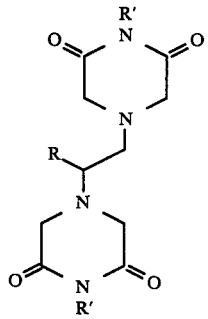

2, R = R' = H
3, R = CH₃, R' = H

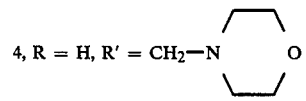

4, R = H, R' = CH₂—N⟨O⟩

Clinical trials with bis(dioxopiperazines) 2 and 3 have been conducted in patients with acute leukemia and lymphosarcoma, as reported in Hellmann, K., Newton, K. A., Whitemore, D. N., Hanham, I. W. F. and Bond, J. V. Br. Med. J. 1969, 1, 822–824. The discovery that the administration of 3 demonstrated considerable leukopenic activity led to further studies and clinical investigations. See, Hellmann, K., Recent Results in Cancer Res. 1970, 30, 52–53; Mathe, G., Amiel, J. L., Hayat, M., de Vassal, F., Schwarzenberg, L., Schneider, M., Jasmin, C. and Rosenfeld, C., Recent Results in Cancer Res. 1970, 30, 54–55; Krepler, P. and Pawlowsky, J., Oesterr Z. Onkol. 1975, 2, 112–114; Bakowski, M. T., Prentice, H. G., Lister, T. A., Malpas, J. S., McElwain, T. J. and Powles, R. L., Cancer Treat. Rep. 1979, 63, 127–129.; Hellmann, K., Newton, K. A. and Humble, J. G. Br. J. Cancer 1978, 37, 479; Bakowski, M. T., Brearley, R. L. and Wrigley, P. F. M., Cancer Treat. Rep. 1979, 63, 2085–2087. Encouraging clinical results in the use of 3 in the treatment of Psoriasis and Kaposi's sarcoma have been reported in Atherton, D. J., Wells, R. S., Laurent, M. R. and Williams, Y. F., Br. J. Dermatol. 1980, 102, 307–317; and Olweny, C. L. M., Sikeywunda, W. and Otin, D., Oncology 1980, 37, 174–176. Further, the clinical evaluation of 3 in combination with radiation therapy has demonstrated a good response in the treatment of various sarcomas. See, Ryall, R. D. H., Hanham, I. W. F., Newton, K. A., Hellmann, K., Brinkley, D. M. and Hjertaas, O. K. Cancer 1974, 34, 1040–1044; Rhomberg, W. U. Int. J. Radiat. Oncol. Biol. Phys. 1978, 4, 121–126; Bates, T., Int. J. Radiat. Oncol. Biol. Phys. 1978, 4, 127–131; Ryall, R. D. H., Int. J. Radiat. Oncol. Biol. Phys. 1978, 4, 133–134; Hellmann, K., Grimshaw, M. B. and Hutchinson, G. E., Int. J. Radiat. Oncol. Phys. 1978, 4, 109–113.

The preparation of the bis(morpholinomethyl) derivative of 2 afforded compound 4, which was found to be active in various experimental tumors as reported in *Science* 1981, 213, 1239. Recent clinical investigations with this compound indicates that it is potentially useful in the treatment of psoriasis, uveitis and malignant lymphomas.

In addition to its antitumor activity bis(dioxopiperazine) 3 has exhibited antimetastatic effects in various tumor models. See, Hellmann, K. and Burrage, K., *Nature (London)* 1969, 224, 273-275; Burrage, K., Hellmann, K., and Salsbury, A. J., *Br. J. Pharmacol.* 1970, 39, 205P-206P; Salsbury, A. J., Burrage, K. and Hellmann, K., *Br. Med. J.* 1970, 4, 344-346; Leserve, A. W. and Hellmann, K., *Br. Med. J.* 1972, 1, 597-601; Salsbury, A. J., Burrage, K. and Hellmann K., *Cancer Res.* 1974, 34, 843-849; James, S. E. and Salsbury, A. J., *Cancer Res.* 1974, 34, 839-842; Kline, I., *Cancer Chemother. Rep. Part 2* 1974, 4, 33-43; Pollard, M., Burleson, G. R. and Luckert, P. H. *The Prostate* 1981, 2, 1-9; Atherton, A. *Eur. J. Cancer* 1975, 11, 383-388; and Lazo, J. S., Ingber, D. E. and Sartorelli, A. C., *Cancer Res.* 1978, 38, 2263-2270.

Further, bis(dioxopiperazine) 3 has been studied to determine possible synergistic effects with other antitumor agents, such as daunorubicin or doxorubicin as reported in Herman, E. H., Mhatre, R. M., Lee, I. P. and Waravdekar, V. S., *Proc. Soc. Ep. Biol. Med.* 1972, 140, 234-239. The dose and time dependence of bis(dioxopiperazine) 3 pretreatment on its protective action against anthracycline-induced toxicity has been studied, as reported in Wang, G., Finch, M. D., Trevan, D. and Hellmann, K., *Br. J. Cancer* 1981, 43, 871-877. Therapeutic synergism of bis(dioxopiperazine) 3 with other antitumor agents has been reported by Woodman R. J., Venditti, J. M., Schepartz, S. A. and Kline I., *Proc. Am. Assoc. Cancer Res.* 1971, 12, 24; Woodman, R. J., Kline, I., and Venditti, J. M., *Proc. Am. Assoc. Cancer Res.* 1972, 13, 31; Woodman, R. J., *Cancer Chemother. Rep. Part 2* 1974, 4, 45-52; Woodman, R. J., Cysyk, R. L., Kline, I., Gang, M. and Venditti, J. M., *Cancer Chemother. Rep. Part 1* 1975, 59, 689-695; Kline, I., *Cancer Chemother. Rep. Part 2* 1974, 4, 33-43; Kline, I., Gang, M. and Venditti, J. M., *Proc. Am. Assoc. Cancer Res.* 1973, 14, 22; and Wampler, G. L., Speckhart, V. J. and Regelson, W., *Proc. Am. Soc. Clin. Oncol.* 1974, 15, 189. In addition, bis(dioxopiperazine) 3 has been reported to potentiate the effects of radiation without simultaneous increase in toxicity. See, Hellmann, K. and Murkin, G. E., *Cancer* 1974, 34, 1033-1039; Peters, L. J. *Br. J. Radiol.* 1976, 49, 708-715; Taylor, I. W. and Bleehan, N. M., *Br. J. Cancer* 1977, 36, 493-500. However, the toxicity patterns of bis(dioxopiperazine) 3 are reported to be similar to those of other antitumor agents. It has been shown that the major toxic effects are leukopenia and reticulocytopenia as reported in Gralla, E. J., Coleman, G. L. and Jonas, A. M., *Cancer Chemother. Rep. Part III* 1974, 5, 1-7. Also, major toxicity was observed in bone marrow, lymphoid tissue and the gastrointestinal mucosa as reported in Levine, B. S., Henry, M. C., Port, C. D. and Rosen, E., *Cancer Treat. Rep.* 1980, 64, 1211-1215. In clinical tests with patients with advanced neoplastic disease, the patients developed hematologic toxicity. Other minor toxic effect observed were thrombocytopenia, nausea and vomiting, diarrhea, and alopecia. See, Creaven, P. J. and Taylor, S. G., *Proc. Am. Assoc. Cancer Res.* 1973, 14, 20; Creaven, P. J., Cohen, M. H., Hansen, H. H., Selawry, O. S. and Taylor, S. G., *Cancer Chemother. Rep.* 1974, 58, 393-400 Bellet, R. E. Mastrangelo, M. J., Dixon, L. M. and Yarbro, J. W. *Cancer Chemother. Rep.* 1973, 57, 185-189. Bis(dioxopiperazines) 2 and 3 have been reported to suppress humoral immunity while having little effect on cell mediated immunity. See, Tucker, D. F. and Finch, M. D., *J. Natl. Cancer Inst.* 1972, 48, 1347-1354; Hellmann, K., *Proc. Roy. Soc. Med.* 1972, 65, 264; Duke, D. L., Field, E. O., Finch, M., Hellmann, K., Tucker, A. S. B. and Tucker, D. F., *Biomedicine* 1973, 18, 199-205; and Dennert, G., Hatlen, L. E. and Tucker, D. F., *J. Natl. Cancer. Inst.* 1975, 54, 621-629.

In addition, the use of bis(dioxopiperazine) 3 has demonstrated schedule-dependent clinical toxicity. Various studies of bis(dioxopiperazines) have suggested possible schedule-dependent pharmacokinetics or mechanism of action. See, Field, E. O., Mauro, F. and Hellmann, K., *Cancer Chemother. Rep.* 1971, 55, 527-530; Sadee, W., Staroscik, J., Finn, C. and Cohen, J., *J. Pharm. Sci.* 1975, 64, 998-1001; Creaven, P. J., Allen, L. M. and Alford, D. A., *J. Pharm. Pharmacol.* 1975, 27, 914-918; Mhatre, R. M., Rahman, A., Raschild, S. and Schein, P., *Proc. Am. Assn. Cancer Res.* 1982, 23, 212; Earhart, R. H., Tutsch, K., Koeller, J. M., Robins, H. I., Davis, H. L. and Tormey, D. C., *Proc. Am. Assn. Cancer Res.* 1982, 23, 128; and Earhart, R. H., Tutsch, K. D., Koeller, J. M., Rodriquez, R., Robbins, H. I., Vogel, C. L., Davis, H. L. and Tormey, D. C., *Cancer Res.* 1982, 42, 5255-5261. Concentrations of 3 in plasma were found to be lower in oral administration compared to the intravenous route, therefore indicating a limiting oral bioavailability, Sadee et al., supra.

The discovery of the cytotoxic effects of bis(dioxopiperazine) 2 initiated a series of structure-activity studies in attempts to obtain more potent and selective agents. (Creighton, 1970, supra.) Compound 2 was prepared as a more lipophilic precursor to the chelating agent 1. Open chain precursors (1, 5 and 6) to 2 did not exhibit cytotoxic properties and the tetraamide 7 has not been evaluated. See, Creighton, A. M. *Progr. Antimicrob. and Anticancer Chemother.* 1970, 1, 167-169 and Leiter, J., Wodinsky, I. and Bourke, A. R., *Cancer Res.* 1959, 19, Part 2, Suppl. 368.

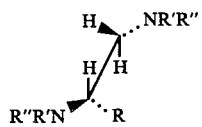

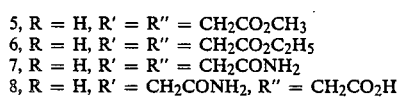

Only minor modifications of the bis(imide) system 2 were allowed to preserve biological activity. The two intact dioxopiperazine moieties were essential for activity. Acyclic amide acid analogue 8 of 2 was not active. Replacement of simple dioxopiperazine rings with others (9-14) also produced inactive compounds.

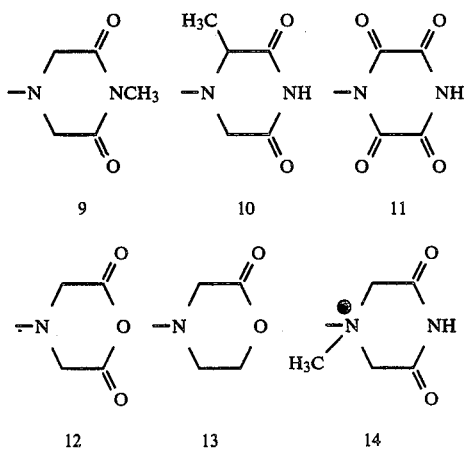

The antitumor activity of bis(dioxopiperazines) was also very sensitive to alterations in the inter-ring alkyl chain. Substitution of a hydrogen in the central ethylene chain of 2 By a methyl group produced a more potent analogue 3. However, replacement of the methyl function by an ethyl group produced inactive 15. Pure enantiomers of 3 were equally active as the racemic compound, but because of solubility advantages (+)−3 is preferred. See, Repta, A. J., Baltezor, M. J. and Bansal, P. C., *J. Pharm. Sci.* 1976, 65, 238–242.

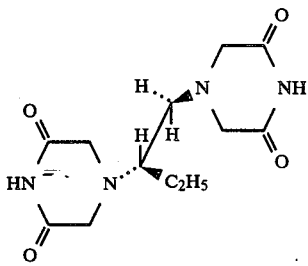

The differences in binding between the intracellular hydrolysis products of 3 and 15 (namely 16 and 17) with various metal ions such as CaII, CuII, FeII, MgII, MnII and ZnII have been examined by Huang, Z. X., May, P. M., Quinlan, K. M., Williams, D. R., and Creighton, A. M. *Agents and Actions* 1982, 12, 536–542.

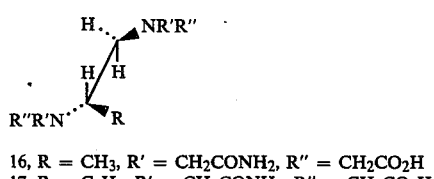

16, R = CH$_3$, R' = CH$_2$CONH$_2$, R" = CH$_2$CO$_2$H
17, R = C$_2$H$_5$, R' = CH$_2$CONH$_2$, R" = CH$_2$CO$_2$H

Variations in the central chain of bis(dioxopiperazine) 2 revealed that the activity declined drastically on homologation of the ethylene chain. Thus, bis(dioxopiperazine) 18 was inactive. Binding of [$^{14}$C]-labelled 18 with cultured mouse embryo fibroblasts have been compared with that of bis(dioxopiperazine) 3 and its precursors 19 as reported in Livingston, D. C., Creighton, A. M. and Fisher, S. W. in "Advances in Antimicrobial and Antineoplastic Chemotherapy," Hejzlar, M., Semonsky, M., Mosak, S., Eds., Univ. Park Press, Baltimore, 1972, Vol. II, pp. 109–110.

Although compound 3 entered the cells very rapidly, the amount of tetraacid 19 absorbed after a 24 hour period was higher than that of 3. On incubation with calf thymus histonenn at 37° C. for 2 hours, a significant association was observed with 3 while the analogue 18 did not show any association under similar conditions. Binding with histones was also not detected with the bis(dioxopiperazine) 2. See, Dawson, K. M., *Biochem. Pharmacol.* 1975, 24, 2249–2253.

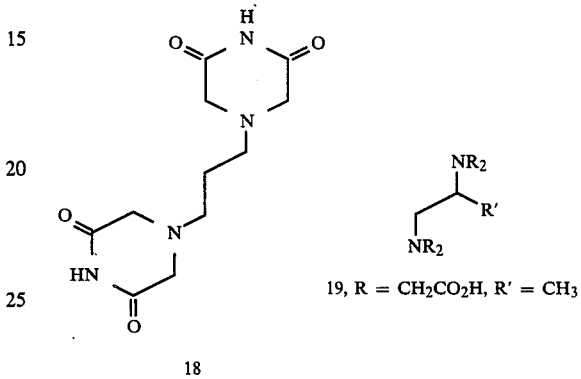

19, R = CH$_2$CO$_2$H, R' = CH$_3$

Substitution of hydrogens on both carbons of the inter-ring ethylene chain of 2 with alkyl groups retained or enhanced activity in cases where the substituents were small and in the erythro or meso configurations. Thus, while compounds 20 and 21 were more cytotoxic than 3, the activity was lost when the number of carbons in the central chain exceeded five. Alkyl chain modified analogues 22–32 (dl-erythro), 33–35 (dl-thero) and 36–38 exhibited a much lower order of activities. See, Creighton, A. M., *Progr. Antimicrob. and Anticancer Chemother.* 1970, 1, 167–169; and Creighton, A. M., Jeffery, W. A. and Long, J. in "Proceedings of the 6th International Symposium on Medicinal Chemistry," Brighton, U. K., Simkin, A., Eds., Sept. 4–7, 1978, pp. 281–288.

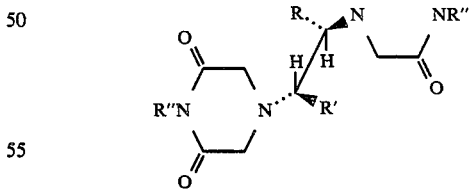

20, R = R' = CH$_3$ R" = H
21, R = CH$_3$, R' = C$_2$H$_5$, R" = H
22, R = H, R' = R" = CH$_3$
23, R = R' = H, R" = CH$_3$
24, R = CH$_3$, R' = nPr, R" = H
25, R = CH$_3$, R' = iPr, R" = H
26, R = CH$_3$, R' = nBu, R" = H
27, R = CH$_3$, R' = CH$_2$OCH$_3$, R" = H
28, R = CH$_3$, R' = Ph, R" = H
29, R = CH$_3$ R' = nBu, R" = H
30, R = CH$_3$, R' = CH$_2$OCH$_3$, R" = H
31, R = CH$_3$, R' = Ph, R" = H
32, R = C$_2$H$_5$, R' = nPr, R" = H

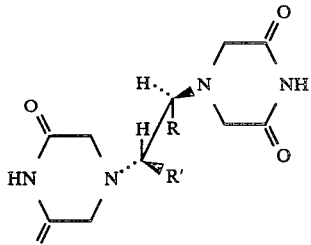

33, R = R' = CH₃ (d1)
34, R = CH₃, R' = CH₂OCH₃
35, R = CH₃, R' = C₂H₅

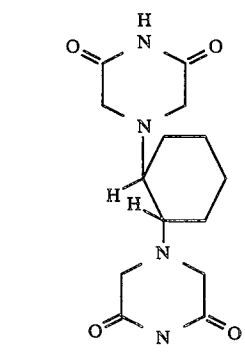

36

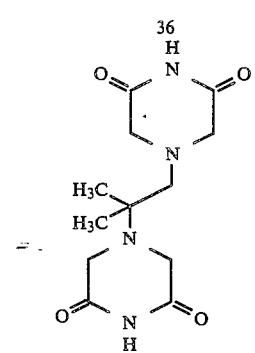

37

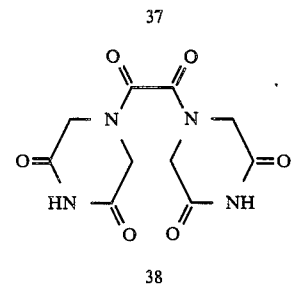

38

A selected number of bis(dioxopiperazines) were examined for their ability to inhibit anthracycline-induced cardiotoxicity, Herman, E. H., El-Hage, A. and Witiak, D. T., *Fed. Proc.* 1982, 41, 1477. Analogues 2, 20, 21 and 23 provided negligible protection. While both 20 and 21 exhibited cytotoxic effects than (+)−3, they also were lethal to animals not treated with daunorubicin. Both optical isomers of bis(dioxopiperazine) 3 exhibited similar protective action against daunorubicin cardiotoxicity.

Stereostructure-activity studies of bis(dioxopiperazines) were conducted in an attempt to establish the preferred geometry for optimum activity. The initial compounds synthesized were the cyclopropyl derivatives (39 and 40) of 3. See, Witiak, D. T., Lee, H. J., Hart, R. W. and Gibson, R. E., *J. Med. Chem.* 1977, 20, 630–635 and Witiak, D. T., Lee, H. J., Goldman, H. D. and Zwilling, B. S., *J. Med. Chem.* 1978, 21, 1194–1197. The cyclopropane ring fixed the geometry of the dioxopiperazine rings either syn or anti to each other. The lipophilicity of 39, 40 and 3 were expected to be similar since the cyclopropyl derivatives differed from 3 only by a mole of hydrogen in molecular weight. However, because of differences in crystal packing, as reported in Hempel, A., Camerman, N. and Camerman, A., *J. Am. Chem. Soc.* 1982, 104, 3456–3458, these compounds exhibited differences in solubility properties.

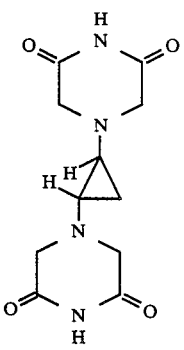

39

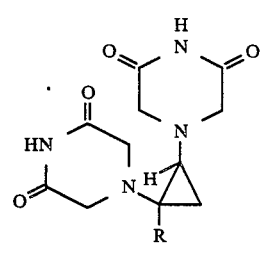

40

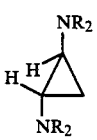

41, R = CH₂CO₂H
42, R = CH₂CO₂CH₃ (HCl salt)

Trans cyclopropyl bis(dioxopiperazine) 39 and its synthetic precursors 41 and 42 were examined and compared with that of bis(dioxopiperazine) 3 and its precursor 19 in V-79A fibroblasts in tissue culture, as reported in Witiak, D. T., Lee, H. J., Hart, R. W. and Gibson, R. E., *J. Med. Chem.* 1977, 20, 630–635. While bis(imide) 3 exhibited cytotoxic effects in this system, trans-39 was nontoxic. The decrease in activity of trans-39 and the reported inactivities of 33 and the trans cyclobutyl bis(imide) 43 in sarcoma 180, leukemia L1210 and [³H]-thymidine assays were thought to be related to similarities in their geometry, Creighton, A. M., *Progr. Antimicrob. and Anticancer Chemother.* 1970, 1, 167–169. The degree of cytotoxicity and mutagencity of 3, 19, 39, 41, and 42 did not follow the same order. The observed order of increasing cytotoxicity was 39<19<4-2<41~3 and that of increasing mutagenicity was $39 < 19 < 41 < 3 \leqq 42$. Thus, bis(imide) 3 was most cytotoxic and mutagenic while the geometrically restricted trans-39 was the least cytotoxic and mutagenic of the compounds. Differences in activities observed between tetraacids 19 and 41 was suggested to be an indication of a mechanism involving asymmetric enzymes, (Troski, J. E. and Hart, R. W., *Interdiscip. Top. Gerontol.* 1976, 9, 168–197) since similar activities were expected if sequestering cations were responsible for their activity. Bis(imide) cis-40 was not examined in the V-79A system and evaluation of cis cyclobutyl analogue 44 has not been reported. Attempted preparation of the precursor (to 44) cis diamine resulted in a violent explosion. (Witiak, D. T., Trivedi, B. K., Campolito, L. B., Reiches, N. A. and Zwilling, B. S., *J. Med. Chem.* 1981, 24, 1329–1332).

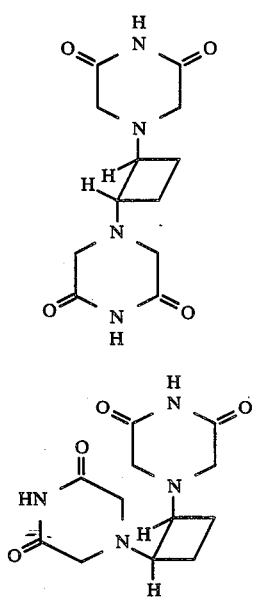

43

44

At concentrations of $10^{-3}$M tetraacid 41 effectively blocked scheduled DNA synthesis, but weakly induced unscheduled DNA synthesis. Other analogues 3, 19 and 39 were less effective in inhibiting scheduled DNA synthesis, but induced unscheduled DNA synthesis dependent on dose.

Bis(dioxopiperazine) cis-40 has been examined for antimetastatic effects in a bronchogenic adenocarcinoma LG1002. Intraperitoneal administration of 3 or cis-40 at doses of 15 mg/kg significantly reduced the number of lung metastases in Syrian golden hamsters compared to the carboxymethylcellulose control. There was no effect on primary tumor growth. Administration of trans-39 (15 mg/kg) stimulated the primary tumor growth and exhibited a greater number of lesions in the lungs than in animals treated with other analogues. Such opposing effects of analogues 39 and 40 were also observed in the B16-F10 melanoma model. See, Zwilling, B. S., Campolito, L. B., Reiches, N. A., George, T. and Witiak, D. T., *Br. J. Cancer* 1981, 44, 578–583. A 24 hour pretreatment of B16-F10 cell line cultures with trans-39 at 2 and 20 μM concentrations increased lung colony formation, while similar treatment with cis-40 reduced lung colony formation. The effect of bis(imide) 3 was similar to that of 40. In vitro results were similar to those observed in vivo except with cis-40. While cis-40 inhibited lung colony formation, in vitro colony formation was stimulated.

Both 39 and 40 also caused an acceleration of the growth of primary tumor. Intermediates 19, 41, 42, 45 or 46 exhibited negligible effects. When tumor cells were pretreated with 3 or cis-40 no primary tumor was established. It was therefore suggested that the inhibition of metastasis may be independent of the angiometamorphic effect of bis(dioxopiperazine) 3. Studies using the F1 cell line which forms few lung colonies compared to the F10 cell line (Fidler, I. J. and Nicolson, G. L., *J.Natl. Cancer Inst.* 1976, 57, 1199–1202) indicated that neither trans-39 nor cis-40 had an effect on lung colony formation in this model.

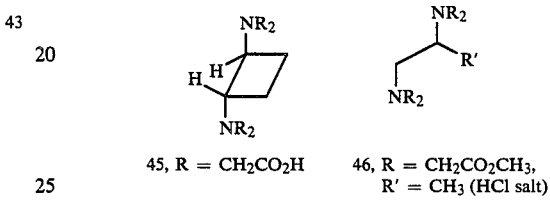

45, R = CH$_2$CO$_2$H    46, R = CH$_2$CO$_2$CH$_3$, R' = CH$_3$ (HCl salt)

Cyclopropyl bis(dioxopiperazine) 39, 40 and intermediates 19, 41, 42, 45, 46 and 47 were examined for protection against daunorubicin cardiotoxicity in hamsters. (Herman, E. H., El-Hage, A. and Witiak, D. T., *Fed. Proc.* 1982, 41, 1477). A 20% survival rate was seen in low dose groups of 45 (21.0 mg/kg) and 47 (21.25 mg/kg). Analogues 46 (88 mg/kg) and 39 (122 mg/kg) were found to be inherently toxic causing 40 and 20% lethality, respectively, in control animals.

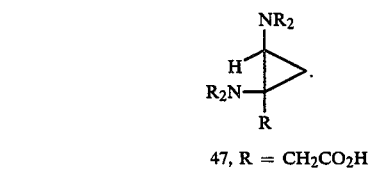

47, R = CH$_2$CO$_2$H

Tricyclic bis(dioxopiperazines) 48 and 49 were examined to determine the geometric preference for activity of bis(dioxopiperazine) 2. Antimetastatic effects of 48, 49 and selected synthetic intermediates (50–52) were studied using the B16-F10 melanoma model as reported with Witiak, D. T., Trivedi, B. K., Campolito, L. B., Reiches, N. A. and Zwilling, B. S., *J. Med. Chem.* 1981, 24, 1329–1332.

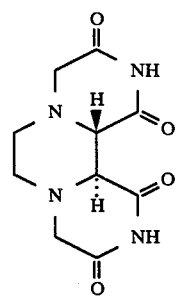

48

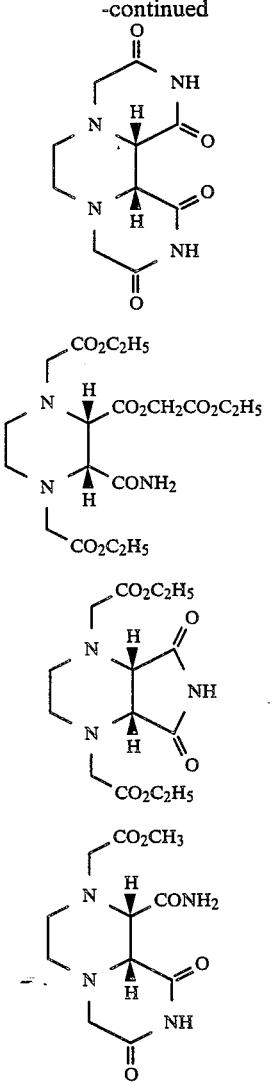

A 24 hour pretreatment of B16-F10 melanoma cells with either trans-48 or tetraester 50 significantly reduced lung colony formation in C57B1/6J mice at all doses studied (2, 20 and 100 μM). Comparison of 48, 49 and 52 revealed that only 48 significantly inhibited metastasis at all doses. Compounds cis-49 and 52 were inactive. Ester imide 51 also exhibited no effect. Inhibition of lung colony formation did not relate to decreased colony formation in vitro. Approximately 50% of the cells were found to form colonies in vitro irrespective of treatment.

Therefore, while there is a current need for a chemotherapeutic agent such as bis(dioxopiperazine) 3, there is a further need for an improved chemotherapeutic agent which does not produce the deleterious and toxic effects associated with bis(dioxopiperazine) 3 such that the improved chemotherapeutic agent can be routinely used as a valuable anticancer drug.

SUMMARY OF THE INVENTION

Bis(dioxopiperazines) 2 and 3 are conformationally flexible about the inter-ring bonds. Among various possible conformations of the dioxopiperazine rings, crystal structure determinations revealed a cis "face to face" conformation of the rings in racemic 3 while the pure enantiomer (+)−3 preferred a trans geometry in which the rings with a parallel arrangement of ring planes were held anti to each other. Similarly, crystal structure determinations of the cyclopropyl analogues 39 and 40 revealed an eclipsed conformation for antimetastatic cis-40, the dioxopiperazine rings being in an orientation similar to that of racemic 3. In the conformationally rigid trans-39 the planes of the dioxopiperazine rings are not parallel as is the case for (+)−3, but exist at an angle of 54°. Thus, while the structures of cis-40 and racemic 3 were exactly superimposable, the fit between (+)−3 and the prometastatic trans-39 was not as good. While cis-40 exhibited a sinusoidal pattern of crystal packing, trans-39 exhibited a more densely packed ribbon pattern, thus accounting for its lower solubility.

Stereoisomeric tricyclic bis(dioxopiperazines) 48 and 49 were synthesized as conformationally restricted analogues of the bis(dioxopiperazine) 2 in which the dioxopiperazine rings of 2 were fixed in a cisoid relationship.

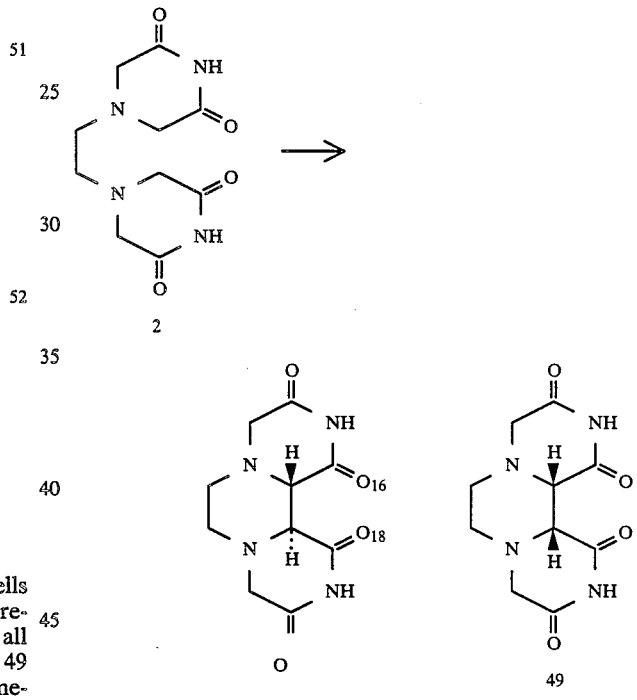

Although such a cisoid relationship of the dioxopiperazine rings was characteristic of the antimetastatic cis-40, in the tricyclic compounds only the trans isomer 48 exhibited antimetastatic effects. Stereoisomer cis-49 was inactive. Crystal structure determinations revealed that although the dioxopiperazine rings had a cisoid relationship in these isomers, they were not oriented "face to face" with each other as found in cis-40 or racemic 3, but existed in a nearly perpendicular arrangement. While the spatial relationships of functional groups and their intramolecular separations were roughly similar in cis-40 and trans-48, there was a significant difference between the inter-ring $O_{16}$-$O_{18}$ separation in cis-40 and cis-49. Thus in cis-49 this distance amounted to 3.07 A° compared to 4.59 and 4.68 A° in trans-48 and cis-40, respectively. Furthermore, the intramolecular distances between $O_{18}$ and other functional atoms in cis-49 were found to be smaller than those in the antimetastatic compounds.

The present invention provides stereoisomeric tricyclic bis(dioxopiperazines) useful as antimetastatic and antitumor drugs. The present invention further provides a process for the synthesis of the stereoisomeric tricyclic bis(dioxopiperazines) 53 and 54.

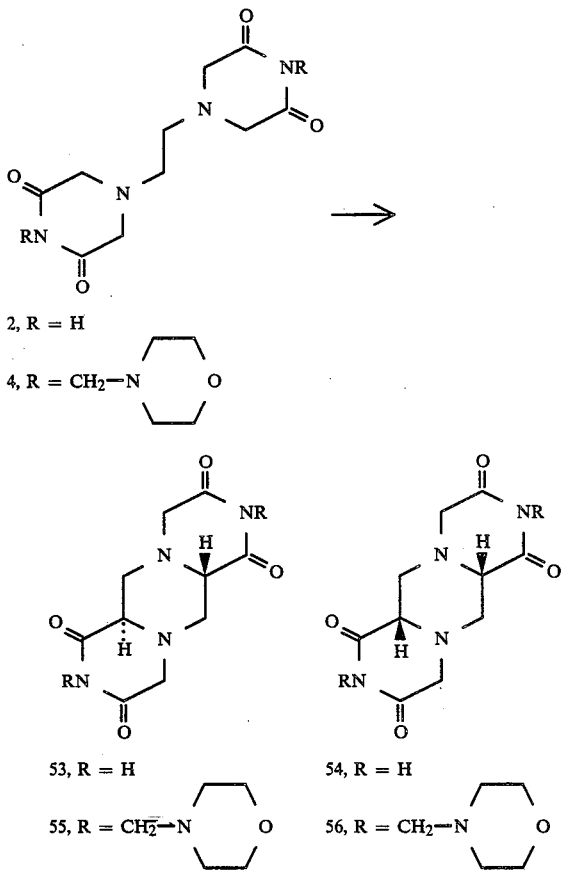

Isomers 53 and 54 are related to bis(dioxopiperazine) 2 and differ from 2 by only one mole of hydrogen in molecular weight. They may be visualized as the regio-isomers of 48 and 49 in which the imide carbonyls bonded to carbon on the central ring have changed position. The present invention also provides the corresponding morpholinomethyl derivatives of 53 and 54 (namely 55 and 56) and their synthesis.

By the present invention it has been discovered that stereoisomeric tricyclic bis(dioxopiperazines) and their bis(morpholinomethyl) derivatives can be quite readily prepared using 2,5-dimethylpyrazine as the starting material. Although such compounds are predictably unstable and undergo hydrolysis to the parent dioxopiperazines, the morpholinomethyl-N groups impart antineoplastic properties to a molecule, owing to their alkylating activities.

The stereoisomeric tricyclic bis(dioxopiperazines) and the morpholinomethyl derivatives thereof were synthesized in order to find an effective anticancer drug which is selected in destroying cancerous cells without damaging other critical tissue.

It has been further discovered that the cis-bis(morpholinomethyl) derivative 56 of the tricyclic bis(dioxopiperazine) is particularly suitable in the inhibition of metastasis in the Lewis Lung carcinoma model. This makes this compound especially suitable as an antitumor or antimetastatic drug.

DESCRIPTION OF BEST AND VARIOUS MODES

Figure 1:
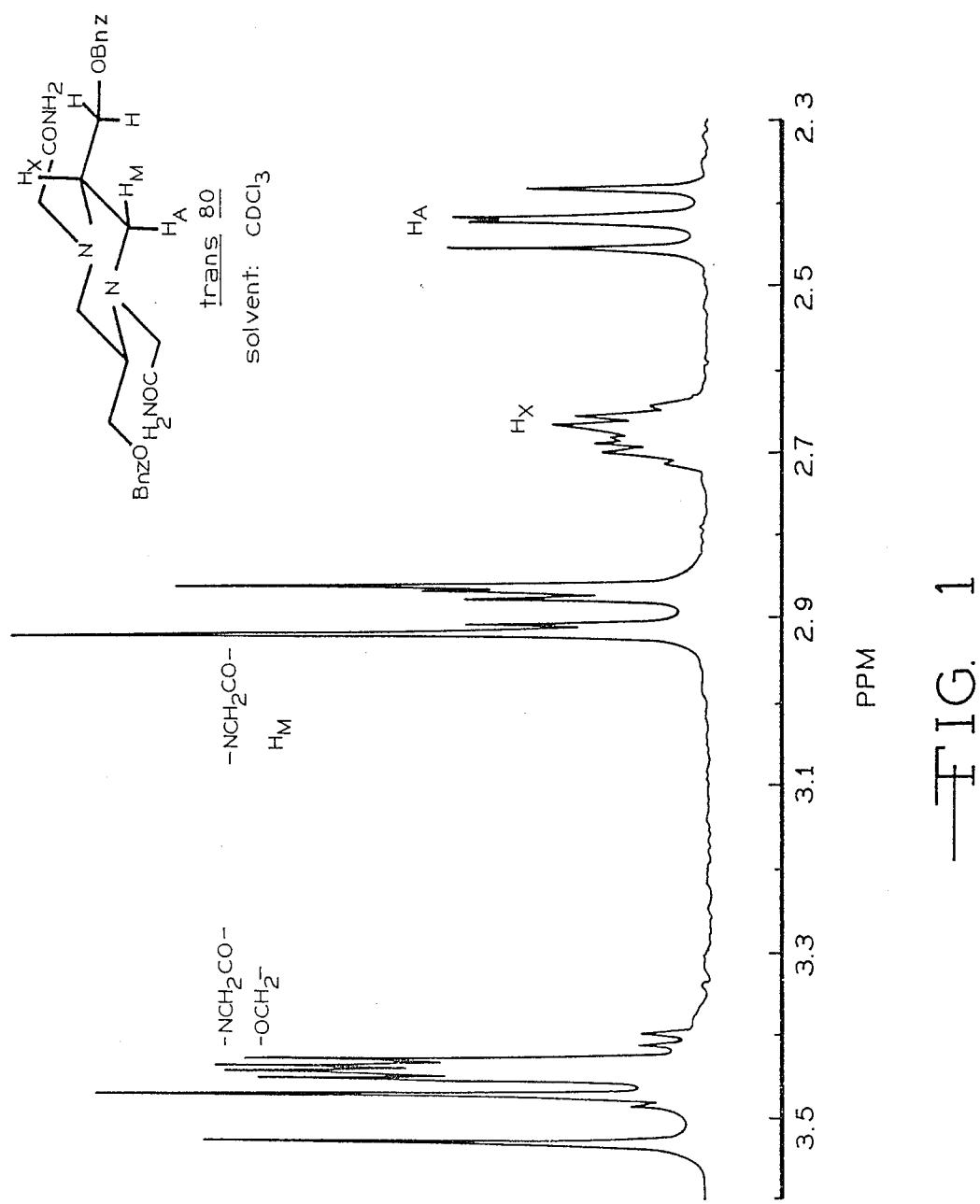
FIG. 1 is a graph showing [$^1$H]—NMR spectrum (300 MHz) showing the piperazine ring proton resonance signals in trans-80.

The first aspect of this invention is a process for the synthesis of stereoisomeric tricyclic bis(dioxopiperazines), 53 and 54, and their bis(morpholinomethyl) derivatives, 55 and 56, which comprises synthesizing pyrazine-2,5-dicarboxylic acid by oxidation of 2.5-dimethylpyrazine using SeO$_2$ in refluxing pyridine-water. Thereafter hydrogenation of an alkaline solution of pyrazine-2,5-dicarboxylic acid at 50°–60° C. and 40–42 psi H$_2$ pressure using Pd/C catalyst to produce the cis- and trans- piperazine-2,5-dicarboxylic acid, and gradual addition of HCl to the alkaline solution to separate the cis- and trans- isomers of piperazine-2,5-dicarboxylic acid. Thereafter refluxing a solution of either the cis or trans piperazine-2,5-dicarboxylic acid in saturated methanol-HCl to produce either the dimethyl cis- or trans-piperazine-2,5-dicarboxylate compound and reacting either the cis- or trans- compound with liquid ammonia under pressure to produce the compound cis- or trans-piperazine 2,5-dicarboxamide. And, finally, reacting the piperazine-2,5-dicarboxamide compound with ethyl bromoacetate/K$_2$CO$_3$ in dimethylsulfoxide at room temperature to produce the diethyl- cis- or trans- 2,5-bis(carbamoyl)-1,4-piperazinediacetate and refluxing either the cis- or trans- compound in ethanol-sodium ethoxide to produce either the cis- or trans-tetrahydrodipyrazino [1,2-a:1′,2′-d]pyrazine-1,3,7,9(2H,4H,8H,10H) tetraone compound of the present invention.

Another aspect of the present invention is the process for the synthesis of the bis(morpholinomethyl) compound which comprises the step of reacting either the cis- or trans- stereoisomeric tricyclic bis(dioxopiperazine) in dimethylsulfoxide with morpholine and formaldehyde to produce either the cis- or trans-tetrahydro-2,8bis(4-morpholinomethyl) dipyrazino[1,2-a:1′,2′-d]-pyrazine-1,3,7,9(2H,4H,8H,10H)-tetrone compound.

In a further aspect of the present invention relates to the cis- and trans- tetrahydrodipyrazine[1,2-a:1′,2-d]pyrazine-1,3,7,9(2H,4H,8H,10H)-tetrone compounds and to the cis- and trans- tetrahydro-2,8-(4 morpholinylmethyl)dipyrazino[1,2-a:1′,1′-d]-pyrazine-1,3,7,9(2H,4H,8H,10H)-tetrone compounds and their uses as effective antitumor or antimetastatic drugs.

A. Synthetic Aspects

A retrosynthetic analysis for construction of stereoisomeric bis(dioxopiperazines) 53 and 54 provides various N,N'bis(alkylated)-2,5-disubstituted piperazines 57-63 as potential precursors. Intermediates 57-63 may be derived from the corresponding 2,5-disubstituted piperazines 64-66.

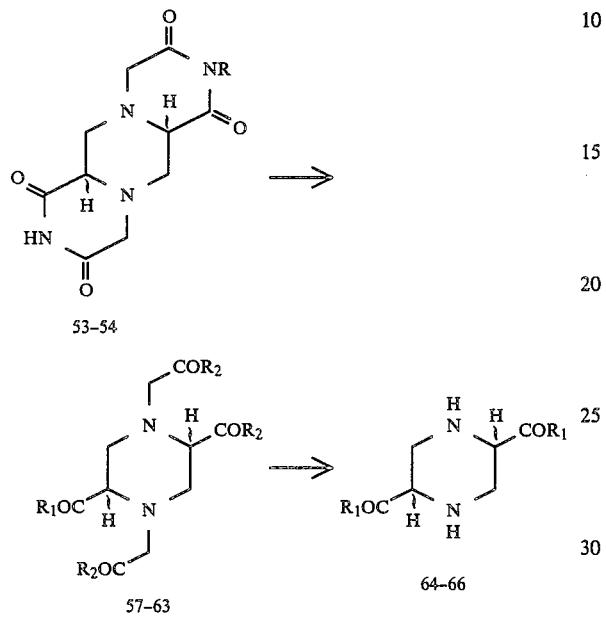

| | | |
|---|---|---|
| 53, trans | 57, $R_1 = R_2 = OH$ | 64, $R_1 = OH$ |
| 54, cis | 58, $R_1 = OH, R_2 = NH_2$ | 65, $R_1 = OCH_3$ |
| | 59, $R_1 = R_2 = OCH_3$ | 66, $R_1 = NH_2$ |
| | 60, $R_1 = OCH_3, R_2 = NH_2$ | |
| | 61, $R_1 = R_2 = NH_2$ | |
| | 62, $R_1 + R_2 = O$ | |
| | 63, $R_1 = NH_2, R_2 = OC_2H_5$ | |

Two approaches were attempted for the preparation of piperazines 64-66. The first involved utilization of appropriately substituted 2,5-dioxopiperazines and the second was based upon reduction of pyrazine dicarboxylates. Thus, in the first approach, selective reduction of the amide functionalities in dioxopiperazine 67 yields dicarboxylate 68.

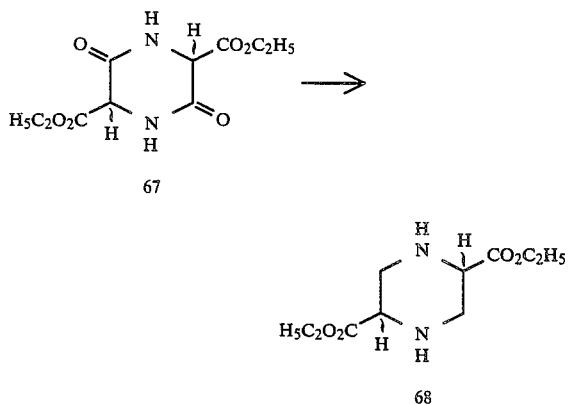

Dioxopiperazine 67 of undefined stereochemistry was reported, in Cheeseman, G. W. H. *J. Chem. Soc. (London)* 1960, 242-247, to be formed on cooling a solution of ethyl aminomalonate (69) in acetone. Hino and Sato, as reported in Hino, T and Sato, T. *Tetrahedron Lett.* 1971, 3127-3129; Hino, T. and Sato, T. *Chem. Pharm. Bull.* 1974, 22, 2866-2874, were unable to dimerize 69 at a temperature of 160°-170° C. Attempts to dimerize this compound failed under a variety of conditions. Ethyl aminomalonate (69) prepared according to the method of Schipper, E. and Day, A. R. *J. Amer. Chem. Soc.* 1952, 74, 350-353, (Scheme 1) underwent slow decomposition even at room temperature, but not dimer could be isolated.

Scheme 1[a]

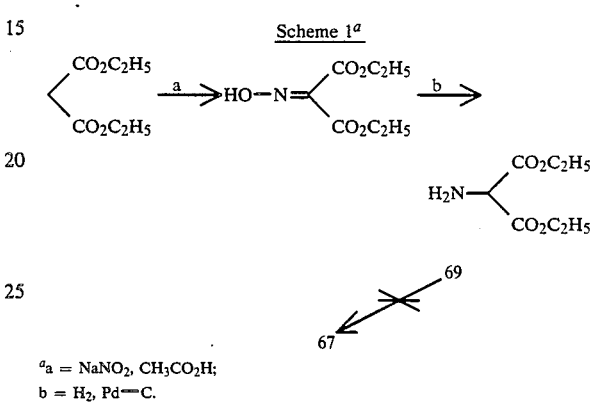

[a] a = $NaNO_2$, $CH_3CO_2H$;
b = $H_2$, Pd—C.

Dioxopiperazine diol 71, a possible precursor to dicarboxylate 68 was investigated. Dioxopiperazine diol 71 was prepared in nearly 77% yield according to the method of Rao and Ravindranath Rao, K. V. and Ravindranath, B. *J. Heterocycl. Chem.* 1975, 12, 147-149, (Scheme II) using commercially available serine methyl ester hydrochloride (70). Thus, hydrochloride 70 was passed through a column of weakly basic anion exchange resin (Amberlite IRA-45) using methanol as eluant and following solvent removal, the resulting free base dimerized at room temperature over a period of 3 days. Geometric isomers were separated by fractional crystallization. The trans isomer was recrystallized from water; the mother liquor on solvent removal yielded crude cis-71 which was recrystallized from methanol. Geometry of these isomers previously had been tentatively assigned based upon melting points, as reported in Roa et al., supra. NMR analysis was not diagnostic for the proposed geometry.

Scheme II[a]

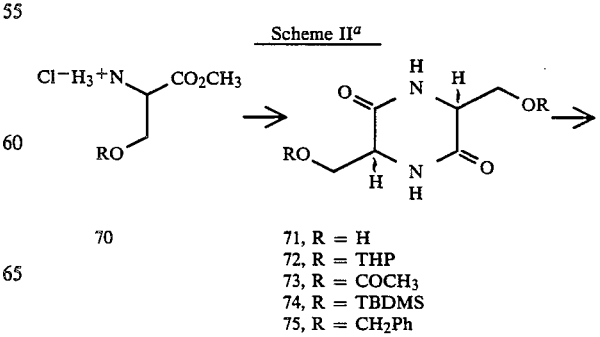

71, R = H
72, R = THP
73, R = $COCH_3$
74, R = TBDMS
75, R = $CH_2Ph$

-continued
Scheme II[a]

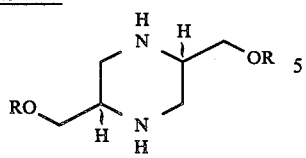

[a] a = Amberlite IRA-45, CH₃OH;
b = R.T., 3 days.

Hydroxyl group protection was necessary for further synthetic work since both geometric isomers of 71 are highly polar and insoluble in most organic solvents. Attempts to prepare THP ethers 72 failed. Cis and trans diacetates 73 were obtained in 78 and 36% yields, respectively, by reaction of pure isomers of 71 with acetyl chloride in acetic acid, but such derivatization did not markedly improve solubility characteristics.

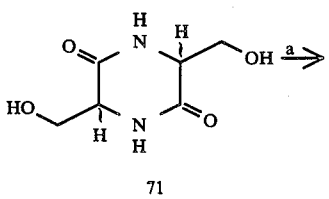

a = CH₃COCl, CH₃CO₂H

Geometric assignments for 73 are tentative. Respective [$^{13}$C]— and [$^{1}$H]—NMR spectra for the pure isomeric esters were nearly identical and thus not useful for defining stereochemistry.

Selective Borch reduction of cis-73, described in Borch, R. F. Tetrahedron Lett. 1968, 61–65, was not successful; reaction of cis-73 with triethyloxonium tetrafluoroborate only afforded nonoiminoether 76 in 25% yield. Bis(iminoether) 77 could not be detected even when using higher reaction temperatures or longer reaction times.

lyl chloride and imidazole in DMF, Corey, E. J. and Venkateswarlu, A. J. Amer. Chem. Soc. 1972, 94, 6190–6191) were not successful.

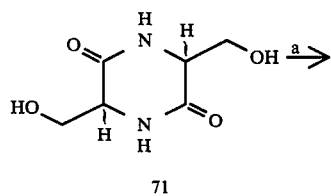

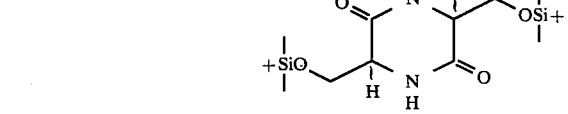

a = TBDMS—Cl, Imidazole, DMF, R.T.

Synthesis of 0-benzyl dioxopiperazine diol 75 from 0-benzyl serine had been described by Russian investigators in Kiryushkin, A. A. Shchelokov, V. I., Antonov, V. K., Ovchinnikov, Yu A. and Shemyakin, M. M. Khim. Prir. Soedin 1967, 3, 267–275 through Chem. Abs. 1968, 69, 77709V. Their procedure involved condensation of 0-benzyl serine with phthalic anhydride prior to aminoacid esterification and subsequent dimerization. However, attempts to produce phthalamide formation only proceeded in poor yields. Alternatively, Fisher esterification of commercially available 0-benzyl-L-serine afforded ester 78 in quantitative yield and chromatography of 78 (Amberlite IRA-45/CH₃OH) followed by solvent removal yielded an oily eluate which dimerized affording a mixture of cis- and trans-75 in 57% yield upon standing at room temperature for 7 days. Although the isomeric mixture could be separated by chromatography (silica gel/CHCl₃), for convenience, this mixture was employed in subsequent reactions. Again, dioxopiperazine geometry could not be assigned from their NMR spectra, but could be confirmed following conversion to the corresponding piperazines 79.

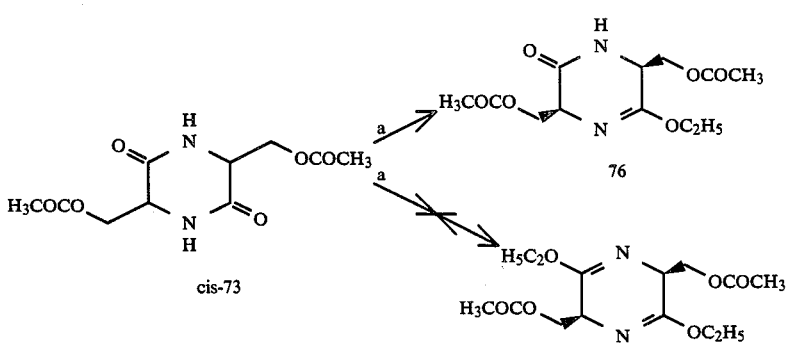

a = Et₃O⁺BF₄⁻, CH₂Cl₂, R.T.

Similarly, attempts to obtain the piperazine from t-butyldimethyl-silyl ethers 74 (prepared in 63–64% yield from pure cis- or trans-71 using t-butyldimethylsi-

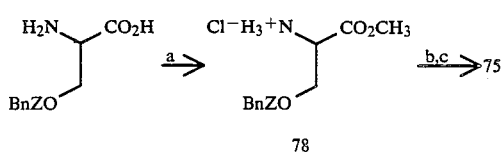

a = CH₃OH, HCl;
b = Amberlite IRA-45, CH₃OH;
c = R.T. 7 days.

LiAlH₄ reduction of diastereomeric 75 afforded the corresponding 2,5-bis(benzyloxymethyl)piperazines 79 which were not purified. When treated with iodoacetamide diastereomers 80 were obtained in 64% overall yield. These isomers (approximately 1:1 ratio) were separated (silica gel/CHCl₃) and their structures confirmed by NMR analysis.

responding pyrazine precursors. Preparation of piperazine-2,5-dicarboxylic acid 64 had been reported in Felder, Von E., Maffei, S., Peitra, S. and Pitre, D., *Helv. Chim. Acta.* 1960, 43, 888–896, from pyrazine diester 83. Hydrolsis of 83 followed by hydrogenation of the alkaline solution at room temperature was reported to afford trans-64, but no evidence for the geometric assignment was provided. Diacid 64 was prepared from the corresponding pyrazine 82. Synthesis of pyrazine-2,5-dicarboxylic acid 82 had been reported by several authors. See Krems, I. J., and Spoerri, P. E., *J. Amer. Chem. Soc.* 1946, 68, 527–528; Mager, H. I. X. and Berends, W., *Rec. Trav. Chim.* 1958, 77, 827–841; Kimura, T., Yamada, S., Kanzahi, K. and Kato, K., *Jpn. Patent* 1960, 10,510 through Chem. ABs. 1961, 55, 9439; Schut, W. J., Mager, H. I. X., and Berends, W., *Rec Trav. Chim.* 1961, 80, 391–398 and Fujii, S., Kikucki, R. and

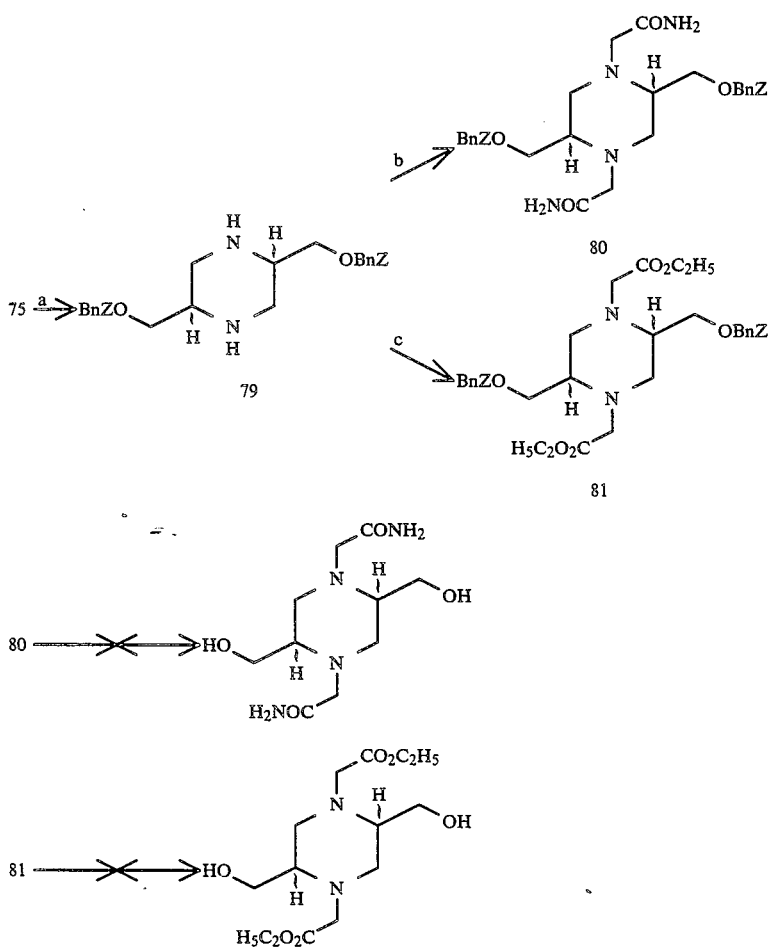

a = LiAl₄, THF, reflux;
b = ICH₂CONH₂, K₂CO₃, C₂H₅OH, R.T.;
c = BrCH₂CO₂C₂H₅, K₂CO₃, C₂H₅OH, R.T.

Attempted debenzylation of diamide 80 using Pd/C, H₂; Pd/C, cyclohexene or 1,4-cyclohexadine; Pd black, 1,4-cyclohexadiene; Na/Liq NH₃ or Me₃SiI were unsuccessful. NMR analysis of the major fractions indicated competing N-dealkylation as well as partial debenzylation. In all cases, starting material could be detected. Similar results were obtained on attempted debenzylation of diester 81 prepared by alkylation of 79 using ethyl bromoacetate.

An alternate pathway for the synthesis of piperazine-2,5-dicarboxylates 64–66 involved reduction of the cor- Kushida, H., *J. Org. Chem.* 1966, 31, 2239–2241. Oxidation using SeO₂ in refluxing pyridine-water afforded 82 in 65–71% yield from commercially available 2,5-dimethylpyrazine. An alkaline solution of diacid 82 at 50°–60° C. and 40–42 psi H₂ pressure using Pd/C catalyst over a period of 12 h afforded an isomeric mixture of 64 in 98% yield. The isomers were separated by crystallization from water under controlled pH. The trans isomer crystallized at pH 5.5–6.5. Further acidification to pH 4.0–5.0 resulted in crystallization of cis-64.

Geometric configurations were assigned by [¹H]—NMR analysis.

iodoacetamide/K₂CO₃ in refluxing ethanol afforded the bis N-alkylated trans bis(imide) 84 in 23% yield.

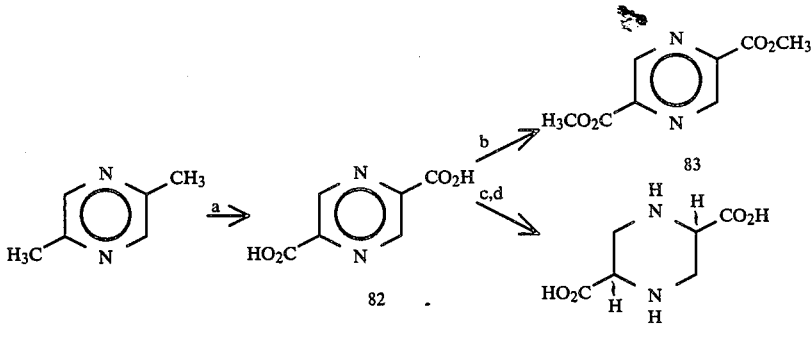

a = SeO₂, Pyridine-water, reflux;
b = CH₃OH, HCl;
c = KOH, H₂O, Pd/C, H₂, 40-42 psi, 50-60° C.;
d = HCl.

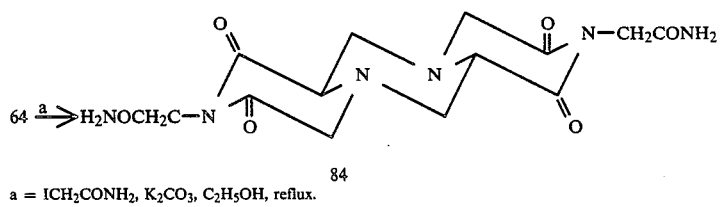

a = ICH₂CONH₂, K₂CO₃, C₂H₅OH, reflux.

Piperazine tetraacids 57 represent simple precursors to the bis(imides) 53 and 54. Reaction of trans diacid 64 with bromoacetic acid in sodium hydroxide/water, afforded good yields (65-75%) of trans tetraacid 57. Reaction of diacid cis-64 under similar reaction conditions was accompanied by partial isomerization. Such isomerization could be prevented if NaOH was replaced by K₂CO₃ in the reaction mixture. Good yields (66% cis, 87% trans) of cis- or trans-57 were routinely obtained. Tetraacids 57 are insoluble in most organic solvents and were purified by redissolving in 10% aqueous Na₂CO₃ solution followed by reacidification (pH 1-2). Recrystallization of cis- and trans-57 could be carried out from water and water:methanol (1:1), respectively, but these procedures resulted in poor recovery.

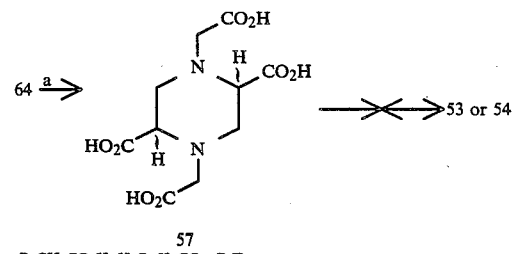

a = BrCH₂CO₂H, H₂O, K₂CO₃, R.T.

Imide formation from diacids may take place upon heating with an equimolar proportion of ammonia or a substituted derivative of ammonia. Such methods involve high reaction temperature; attempted reactions using ammonia, urea, or formamide resulted in decomposition of 57. No bis(imide) 53 or 54 could be isolated.

In an attempt to obtain the diacid diamide 58, another possible precursor to bis(imides) 53 and 54, reaction of an isomeric mixture of diacid 64 and excess The trans geometry of 84 was characterized by the geminal and diaxial couplings exhibited by the axial proton of the central ring methylene proton resonance signal which appeared as a deceptively simple triplet (doublet of doublets, δ2.29 ppm) in the [¹H]—NMR spectrum. Although bis(imide) 53 or 54 was not isolable under similar reaction conditions using fewer equivalents of iodoacetamide, reaction of trans-64 and chloroacetamide/K₂CO₃ at room temperature in water followed by acidification to pH 1-2 using conc. HCl provided the trans diacid diamide 58 in 66% yield. Cis-58 could not be prepared under similar reaction conditions.

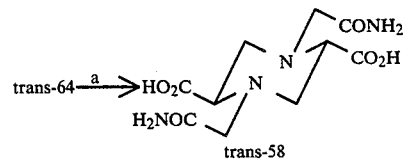

a = ClCH₂CONH₂, K₂CO₃, H₂O, R.T.

Refluxing in acetic anhydride, heating neat, use of DCC or heating in acidic solvents (CH₃CO₂H, H₂SO₄ or polyphosphoric acid) did not effect cyclization of trans-58 to trans-53. While Fisher esterification of trans-58 afforded tetraester trans-59, other methods of esterification as reported in Arai, I., and Muramatsu, I., *J. Org. Chem.* 1983, 48, 121-123; Mohacsi, E., *Synth. Commun.* 1982, 12, 453-456; and Rachele, J. R., *J. Org. Chem.* 1963, 28, 2898, did not produce the desirable amide ester trans-60 presumably owing to the insoluble nature of trans-58. Both cis and trans tetraesters 59 were also obtained in good yields (69-74%) from Fisher esterification of the corresponding tetraacids 57.

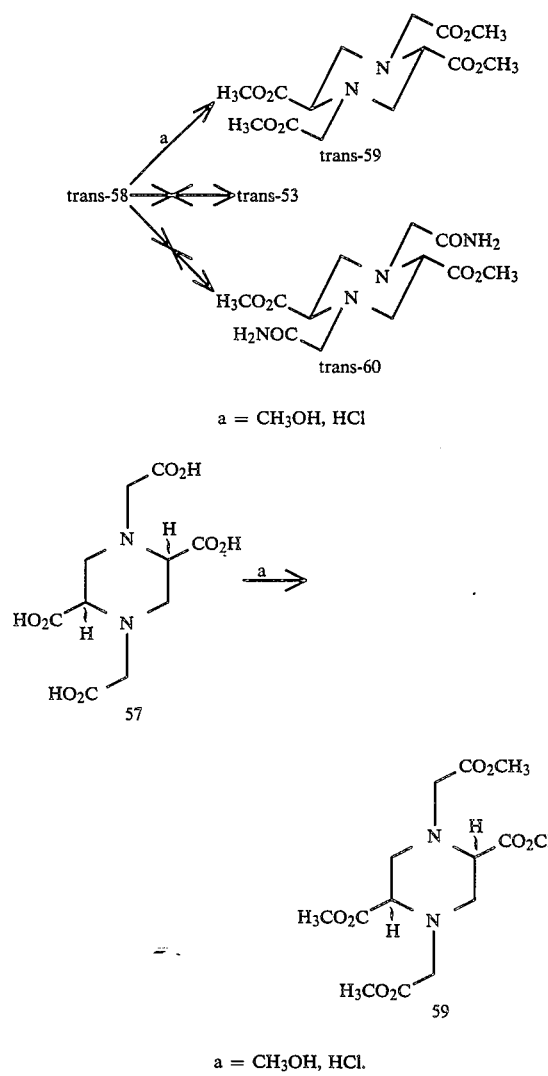

a = CH₃OH, HCl

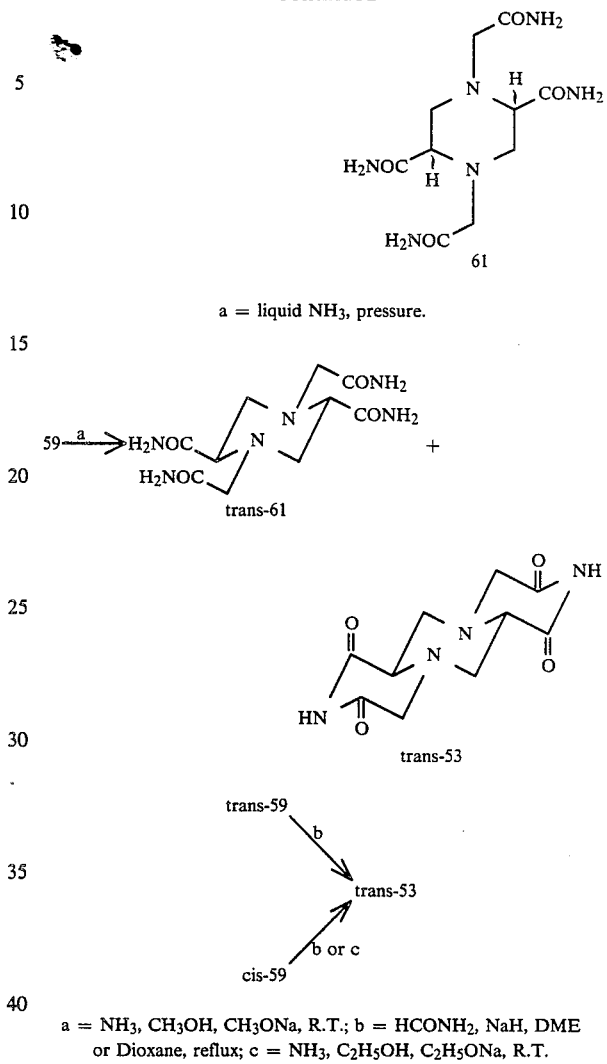

a = NH₃, CH₃OH, CH₃ONa, R.T.; b = HCONH₂, NaH, DME or Dioxane, reflux; c = NH₃, C₂H₅OH, C₂H₅ONa, R.T.

Tetraester trans-59 is a crystalline solid whereas the cis isomer is a colorless oil which turns yellow on standing at room temperature. Both tetraesters are soluble in organic solvents and afforded excellent yields of the corresponding tetraamides 61 on reaction with liquid ammonia under pressure. Reaction of either isomer and ammonia in methanol and sodium methoxide at room temperature also afforded the tetraamide trans-61 as the major product along with small amounts (≦16%) of the bis(imide) trans-53.

Heating trans- or cis-59 with formamide failed to produce bis(imide) 53 or 54, but reaction with formamide in the presence of NaH/refluxing dimethoxyethane or dioxane afforded trans-53 as the exclusive product in about 25% yield. With cis-59, use of sodium ethoxide in ethanol-ammonia only afforded trans-53 (30% yield). Heating either the cis- or trans-tetraamide 61 in polyphosphoric acid at 85° C. for 15 to 30 min produced small amounts (10–15%) of trans-bis(dioxopiperazine) 53; decomposition of the reactants was predominant.

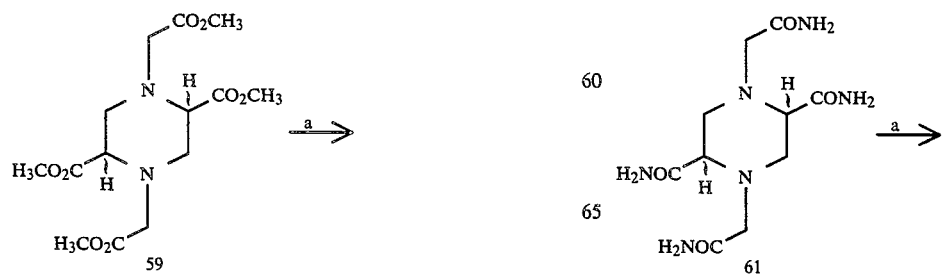

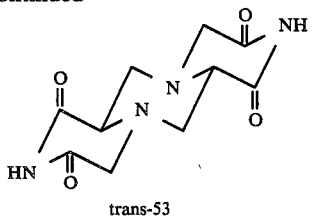

trans-53 a = PPA, 85° C.

Alternative possibilities for preparation of imides involve anhydride precursors. Refluxing tetraacid cis-57 in acetic anhydride afforded epimerized trans-62 (72% yield) which was identical in all respects to trans-62 prepared from trans-57 under similar reaction conditions. Use of lower reaction temperatures or DCC also did not provide cis-62 in isolable quantity.

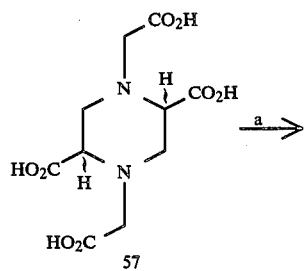

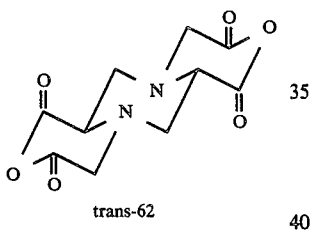

trans-62 a = acetic anhydride, reflux.

Amide esters may be cyclized in the presence of sodium alkoxides, alkalis or alkali metals in nonaqueous media and at moderate temperatures to afford imides. Since cis- or trans-60 could not be isolated by alkylation of either stereoisomer of diester 65, the use of amide ester 63 as the immediate precursor to 53 and 54 was carried out.

Pyrazine-2,5-diamide 85, prepared according to a published procedure by Spoerri, P. E. and Erickson, A., J. Amer. Chem. Soc. 1938, 60, 400-402, was insoluble in most organic solvents and attempted reduction to afford piperazine 66 was not successful under various conditions. Alternatively, refluxing a heterogeneous solution of trans-64 in saturated methanol-HCl afforded diester trans-65 in 47.6% isolated yield. Unreacted diacid 64 was recycled resulting in an overall conversion of 67%. Fisher esterification of methanol-HCl soluble cis-64 afforded diester cis-65 in 69% yield. This esterification was accompanied by partial isomerization; trans-65 hydrochloride precipitated as the reaction progressed (1.5-2 h). Neutralization of this solid (20% Na2CO3 solution) followed by solvent extraction (CHCl3) afforded trans-diester 65 (4.9%). Other esterification methods, (Arai, I. and Muramatsu, I., J. Org. Chem. 1983, 48, 121-123; Rachele, J. R., J. Org. Chem. 1963, 28, 2898), were not successful. Hydrogenation of diester 83 obtained on Fisher esterification of 82 also failed to yield 65 under a variety of conditions. Diester trans-65 could be recrystallized from acetone-hexane, but recovery was poor. Cis-65 was obtained as a viscous oil which solidified in vacuo over several hours. Both isomers are soluble in water as well as most organic solvents and afforded excellent yields of corresponding diamides 66 on reaction with liquid ammonia under pressure. Reaction at atmospheric pressure or other literature procedures as discussed in Spoerri, P. E. and Erickson, A., J. Amer. Chem. Soc. 1938, 60, 400-402, afforded only poor yields of 66.

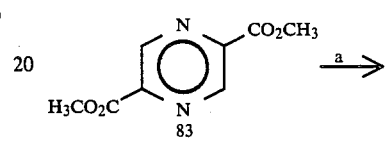

a = CH3OH, NH3, reflux.

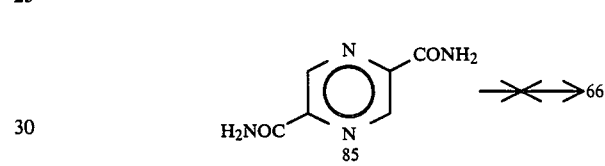

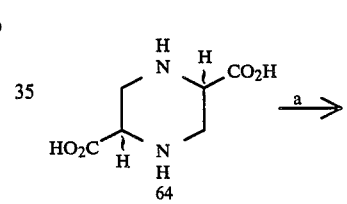

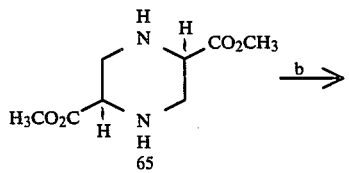

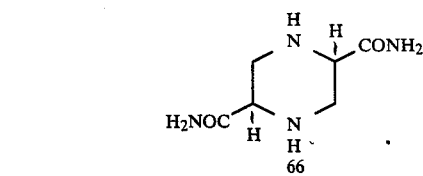

a = CH3OH, HCl; b = liquid NH3, pressure.

Amide esters cis- and trans-63 were obtained in 40 and 84% yields, respectively, by reaction of the corresponding diamides and ethyl bromoacetate/K2CO3 in DMSO at room temperature. While trans-63 was insoluble in water and most organic solvents, the cis isomer was water soluble. Refluxing trans- or cis-63 in ethanol-sodium ethoxide afforded the corresponding bis(imides) 53 or 54 in 71-89% yield.

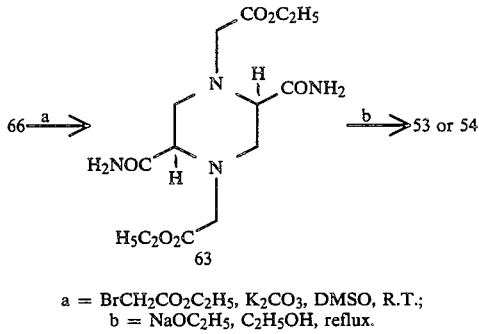

a = BrCH₂CO₂C₂H₅, K₂CO₃, DMSO, R.T.;
b = NaOC₂H₅, C₂H₅OH, reflux.

Conversion to the corresponding bis(morpholinomethyl) derivatives 55 and 56 took place in DMSO in the presence of morpholine and formaldehyde.

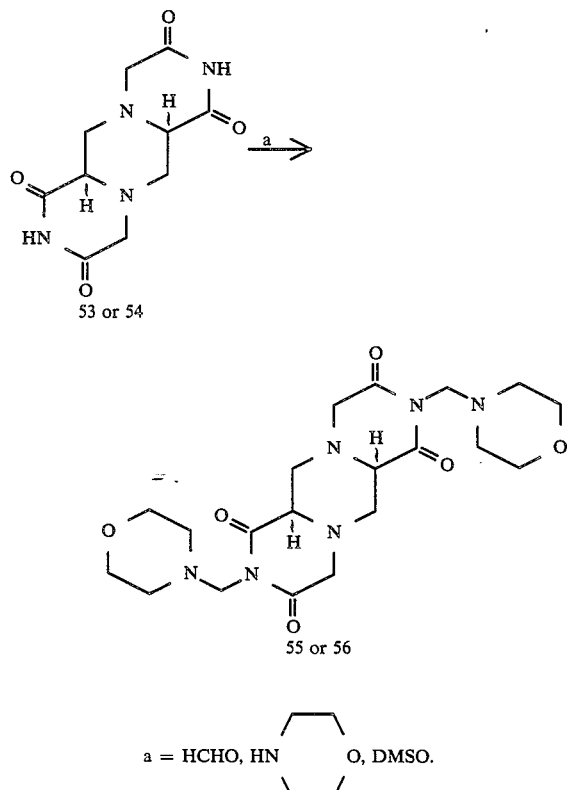

a = HCHO, HN⌐O, DMSO.

B. [¹H]—NMR Spectral Analysis

Figure 2:
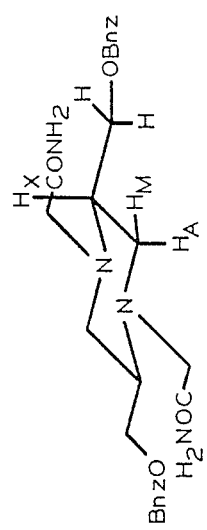
FIG. 2 is a graph showing decoupled [$^1$H]—NMR spectrum (300 MHz) of trans-80.
Figure 2:
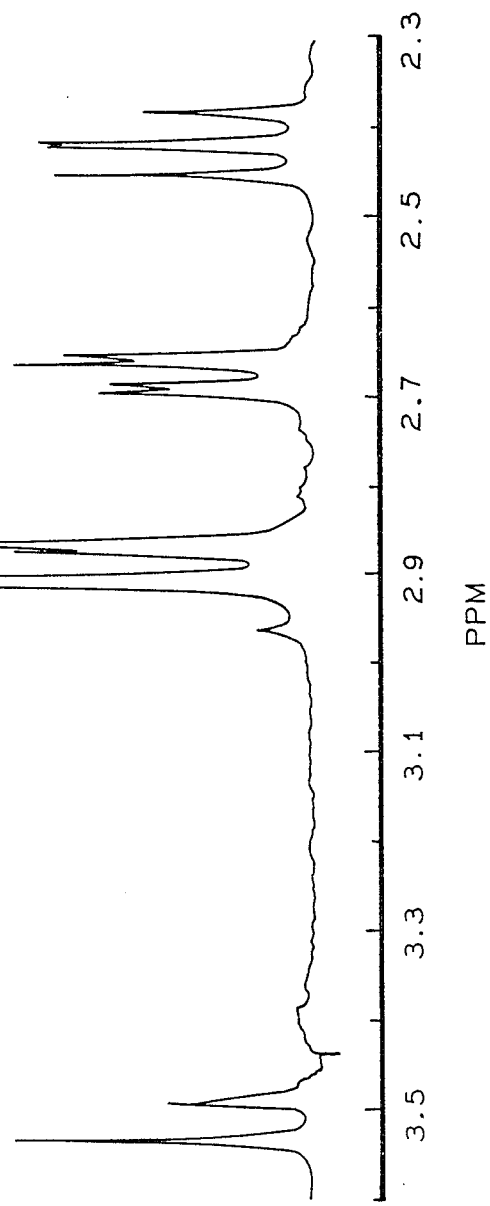
Figure 3:
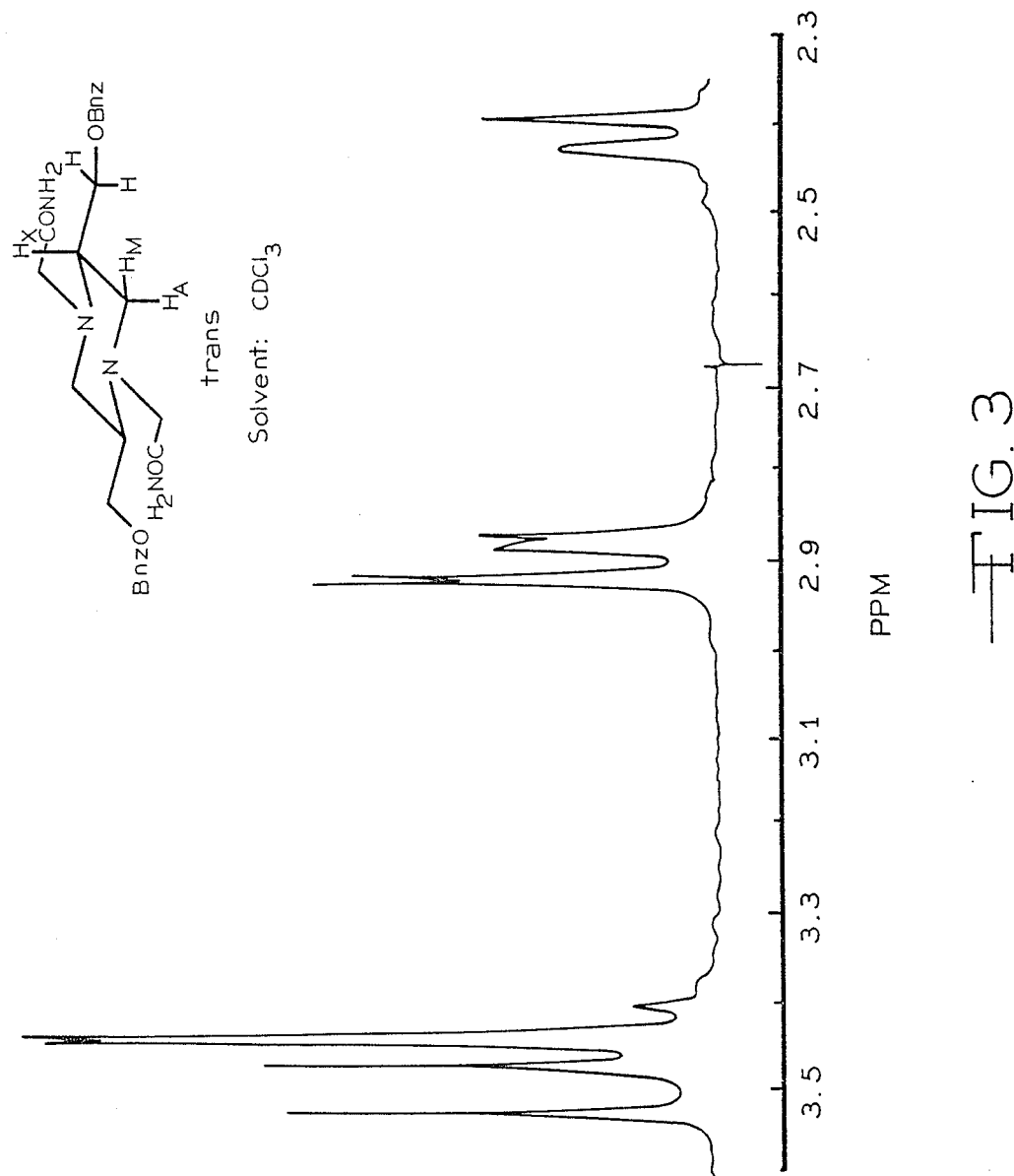
FIG. 3 is a graph showing decoupled [$^1$H]—NMR spectrum (300 MHz) of trans-80.
Figure 4:
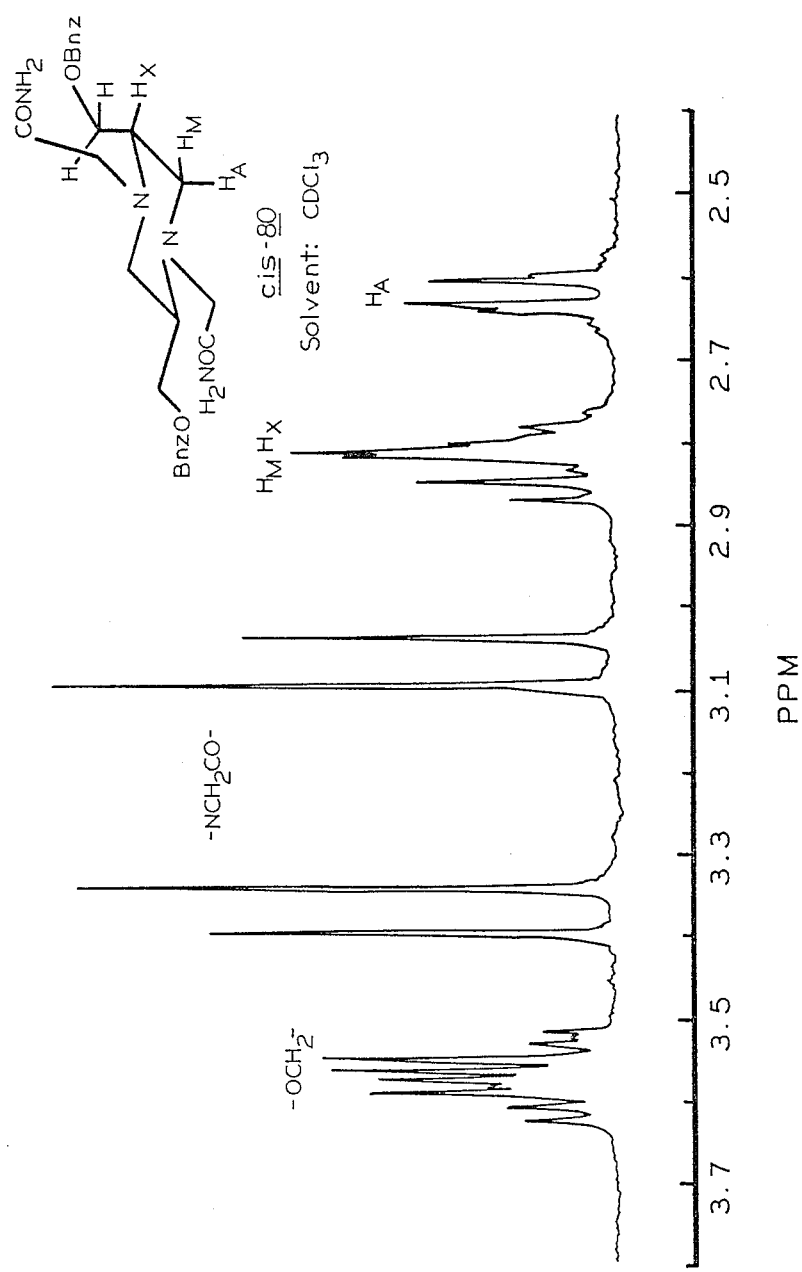
FIG. 4 is a graph showing [$^1$H]—NMR spectrum (300 MHz) showing the piperazine ring proton resonance signals in cis-80.

The 300 MHz proton resonance spectra for piperazines cis- and trans-80 found in FIGS. 1-5 were particularly useful for geometric assignments. Piperazine protons of trans-80 exhibited an AMX pattern of resonance signals (FIG. 1) wherein the signal centered at δ 2.42 was assigned to the $H_A$ axial proton of the methylene group. The axial conformation for $H_A$ was assigned based on the observed gemial ($|J_{AM}| = 11.4$ Hz) and diaxial ($J_{AX} = 9.9$ Hz) coupling constants. The $H_M$ equatorial resonance signal of the methylene group centered at δ 2.89 was masked by the geminally coupled $H_{A^*}$ signal of $A^*X^*$ in —NCH₂CO—. The $H_{X^*}$ resonance signal of this function is centered at δ 3.50 ($|J_{A^*X^*}| = 17.0$ Hz). The $H_X$ signal (δ 2.67) of AMX was complicated by additional coupling to the exocyclic methylene group of —CH₂O—Bnz. Irradiation of these exocyclic methylene resonance signals revealed the $J_{AX}$ diaxial coupling and $J_{MX} = 2.8$ Hz for equatorial-axial coupling (FIG. 2). Irradiation of the $H_X$ resonance signal revealed $|J_{AM}|$ geminal coupling (FIG. 3).

Figure 5:
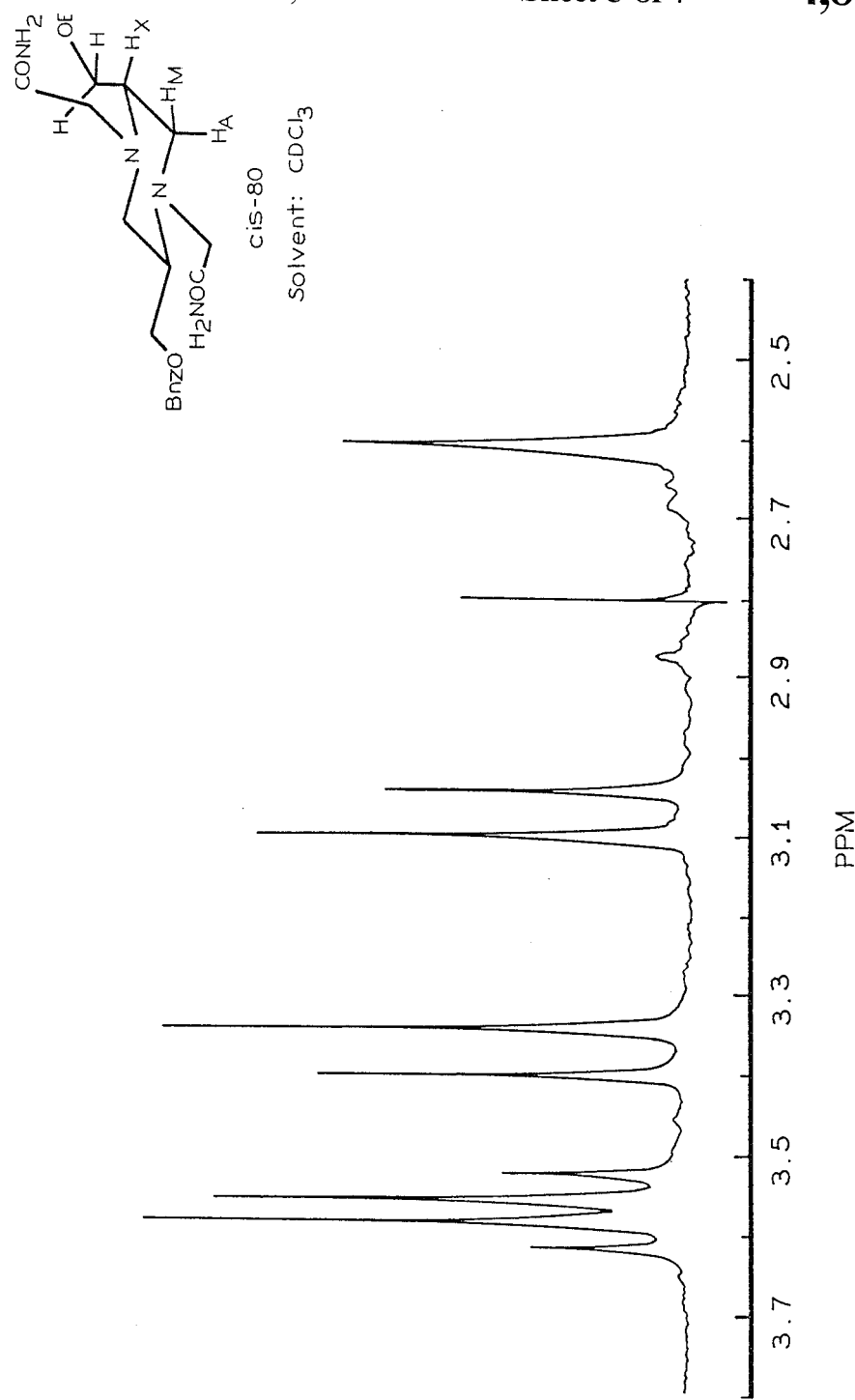
FIG. 5 is a graph showing decoupled [$^1$H]—NMR spectrum (300 MHz) of cis-80.

For cis-80 (FIG. 4) the $H_A$ axial proton resonance signal (δ 2.62) exhibited $|J_{AM}| = 10.6$ Hz (geminal) and $J_{AX} = 2.0$ Hz (axial-equatorial). The resonance signals for $H_M$ and $X_X$ overlapped providing a complex multiplet (δ 2.8–2.9). Irradiation of the $H_M$—$H_X$ multiplet collapsed the $H_A$ resonance signal to a singlet and revealed geminal coupling ($|J| = 9.8$ Hz) for the exocyclic methylene in —CH₂O—Bnz (FIG. 5). Whereas in trans-80 (FIG. 1) the geminally coupled —NCH₂CO—resonance signals appeared as an A*X* pattern, in cis-80 (FIG. 4) the coupling pattern approached that of an A*B* system ($δ_{A^*}$ 3.07, $δ_{B^*}$ 3.36, $J_{A^*B^*} = 17.0$ Hz).

Figure 6:
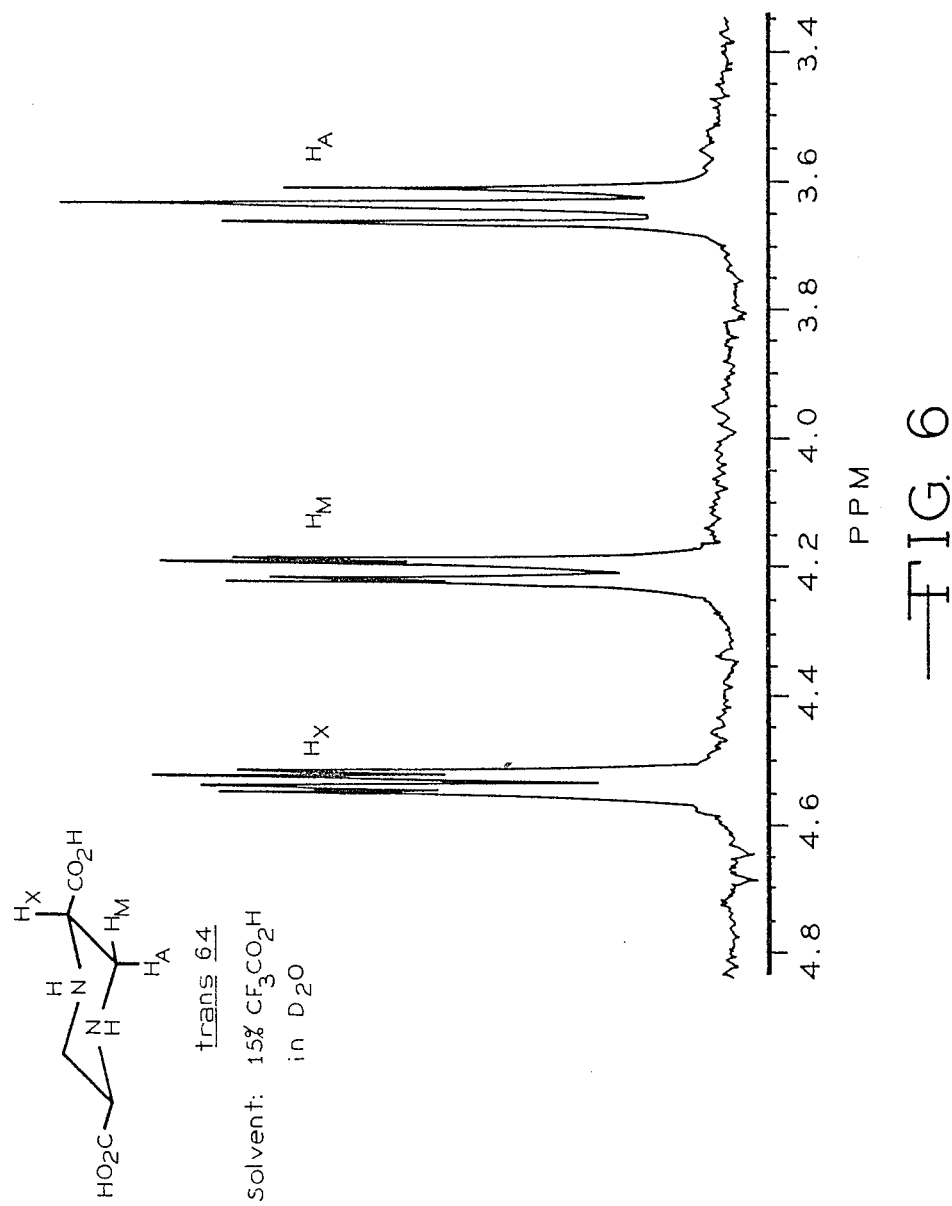
FIG. 6 is a graph showing [$^1$H]—NMR spectrum (500 MHz) of trans-64.

Characterization of geometric tricycles 53 and 54 was based in part upon analysis of the 500 MHz proton NMR spectrum of precursor piperazine-2,5-dicarboxylic acids cis- or trans-64. Epimerization, if any, only occurred during esterification of cis-64; trans ester 65 (<5%) could easily be separated from the reaction mixture. As observed for trans-80 the piperazine ring proton resonance signals for trans-64 exhibited an AMX pattern (FIG. 6). The axial $H_A$ resonance signal (δ 3.64) is deceptively simple. $|J_{AM}| = 14.1$ Hz (geminal) and $J_{MX} = 3.8$ Hz (axial-equatorial) were derived by analysis of the $H_M$ signal (δ 4.21). $J_{MX}$ and $J_{AX} = 12.4$ Hz (axial-axial) were observed in the $H_X$ resonance signal (δ 4.53).

Figure 7:
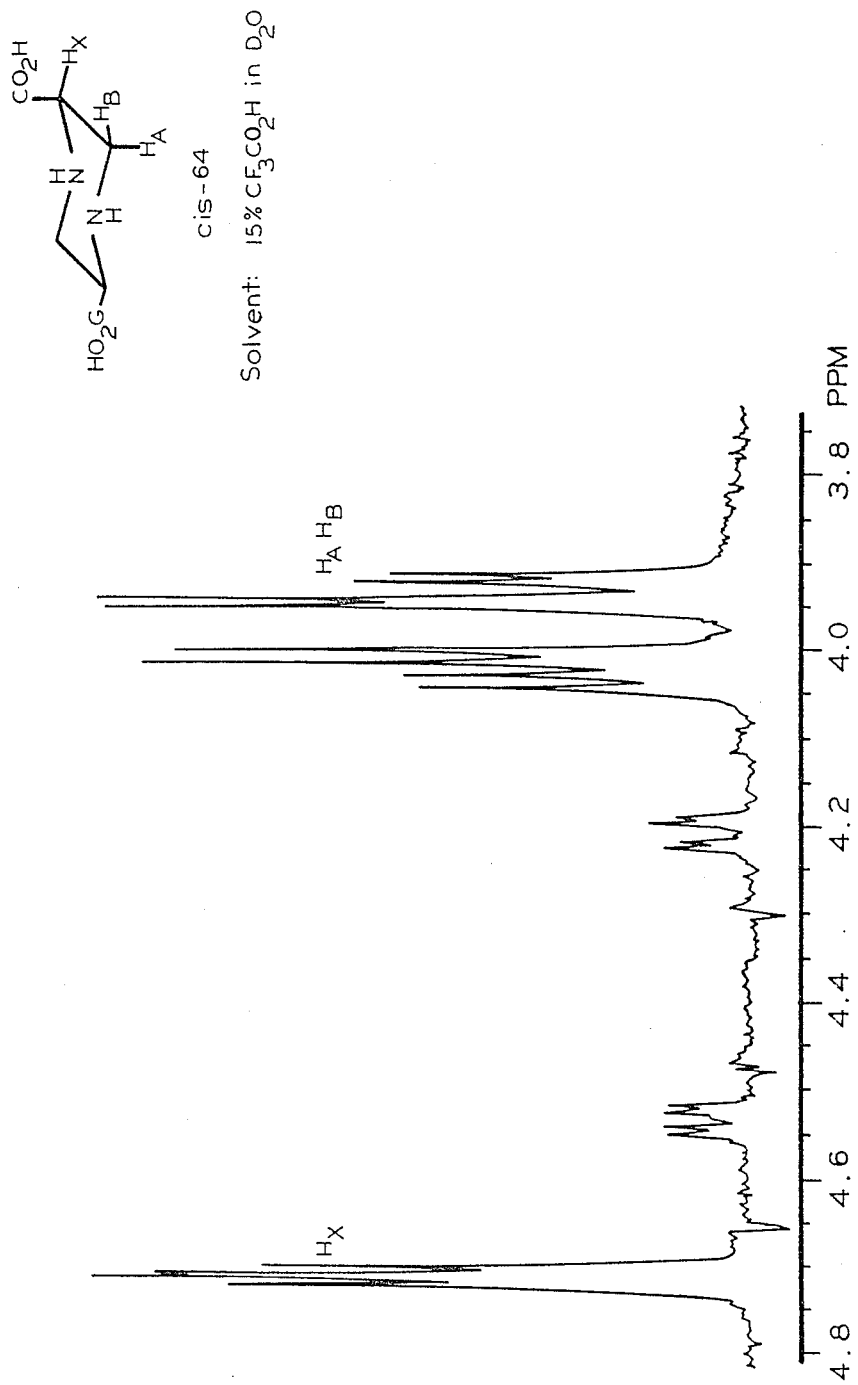
FIG. 7 is a graph showing [$^1$H]—NMR spectrum (500 MHz) of cis-64.

For cis-64, which rapidly interconverts on the NMR time scale, an ABX pattern was observed for the piperazine proton resonance signals (FIG. 7) wherein calculated constants were $δ_A$ 3.93, $δ_B$ 4.02, $J_{AX} = 4.4$ Hz and $J_{BX} = 7.1$ Hz with $δ_X$ (observed) 4.71 and $|J_{AB}|$ (observed) = 14.5 Hz (geminal). Splitting patterns similar to those observed for cis- and trans-64 were observed, respectively, for cis and trans diesters 65 and diamides 66 and the diester-diamide trans-63. The cis diester-diamide 63 provided a first order spectrum at 90 MHz which was in agreement with the proposed structure. Relative to tricyclic bis(dioxopiperazines) the spectrum of trans-53 exhibited a characteristic deceptively simple triplet for the $H_A$ axial proton (δ 2.18) of the central ring methylene group not unlike that observed for the equivalent proton resonance signal in piperazine diacid precursor trans-64. The cis isomer 54 exhibited a spectrum (90 MHz) wherein the axial $H_A$ and equatorial $H_B$ resonance signals appeared as broad multiplets between δ 2.7–2.9. Thus, NMR analysis of intermediates provide for geometric assignments of tricyclic targets 53 and 54.

Melting points were determined in open capillaries with a Thomas-Hoover Uni-Melt apparatus and are uncorrected. Infrared spectra were recorded with a Beckman model 4320 spectrophotometer. Nuclear magnetic resonance spectra were recorded using either a Bruker WP-80, HX-90E, 300 MHz or a Nicolet 500 MHz spectrophotometer. TMS (CDCl₃, DMSO, pyridine-d₅) or TSP (D₂O) were used as internal standards unless otherwise specified. Chemical shifts are reported on the δ scale with peak multiplicities: c, complex; d, doublet; dd, doublet of doublets; m, multiplet; q, quartet; s, singlet; and t, triplet. Mass spectra were recorded with a DuPont model 21-491 mass spectrometer with a model 21-094 data system.

Ethyl Aminomalonate (69) was prepared by the procedure of Schipper, E. and Day, A. R., *J. Amer. Chem. Soc.* 1952, 74, 350–353.

cis- and trans-3,6-Bis[(hydroxy)methyl]piperanzine-2,5-dione (71) were prepared by the procedure of Rao and Ravindranath, supra. A solution of DL-serine methyl ester hydrochloride (15 g, 0.096 mol) in methanol (150 ml) was passed through a column (3×52 cm) of weak base type ion exchange resin (Amberlite IRA-45, 16-50 mesh) which was previously washed with 5% aqueous sodium bicarbonate solution (750 ml) followed by water (900 ml) and methanol (600 ml). The effluent and the methanol wash (300 ml) were concentrated under reduced pressure to yield an oil which was kept at room temperature for 3 days. The solid formed was triturated with a mixture of methanol and ether (1:1) and filtered to afford 6.4 g (76.9%) of 71 which was recrystallized from hot water to yield 1.9 g (22.7%) of trans isomer mp 272°–273° C. (lit. Rao et al., supra. mp 284°–285° C.). The mother liquor on evaporation under reduced pressure yielded the crude cis isomer which upon recrystallization from methanol afforded 2.64 g (31.45%) of white crystals mp 226°–228° C. (lit. Rao et al., supra., mp 228°–230° C.).

cis-3,6-Bis[(acetyloxy)methyl]piperazine-2,5-dione (73) was prepared using methodology similar to the methodology used for the preparation of the chloroacetyloxy analogue (Rao, et al., supra). A mixture of cis-71 (1.0 g, 5.75 mmol), acetyl chloride (1.8 ml, 25.1 mmol) and glacial acetic acid (2.5 ml) was stirred at room temperature for 5 hours. An additional 2.5 ml of acetic acid was added at the end of 1.5 hours. The mixture was diluted with acetone, filtered and recrystallized from methanol yielding 1.15 g (77.7%) of white crystals mp 227°–228° C.; IR (KBr) cm$^{-1}$ 1755 (ester), 1685 (amide); NMR (DMSO-$d_6$, 90 MHz) δ 2.04 (s, 6H, COCH$_3$), 4.21 (s, br, 6H, OCH$_2$CH), 8.42 (s, 2H, CONH). Anal. calcd. for C$_{10}$H$_{14}$N$_2$O$_6$: C, 46.51; H, 5.47; N, 10.85. Found: C, 46.31; H, 5.54; N, 10.74.

trans-3,6-Bis[(acetyloxy)methyl]piperazine-2,5-dione (73) was prepared using methodology similar to that employed for the preparation of the chloroacetyloxy analogue, Rao, et al., supra. A mixture of trans-71 (1.0 g, 5.75 mmol), acetyl chloride (1.8 ml, 25.1 mmol), acetic acid (5 ml) and 10 drops of sulfuric acid was stirred for 2 days at room temperature with occasional warming. The mixture was diluted with water, filtered and recrystallized from methanol yielding 0.53 g (35.8%) of white crystals mp 237°–238° C.; IR (KBr) cm$^{-1}$ 1740 (ester), 1680 (amide); NMR (DMSO-$d_6$, 90 MHz) δ 2.02 (s, 6H, COCH$_3$), 4.22 (s, br, 6H, OCH$_2$CH), 8.37 (s, 2H, CONH). Anal. calcd. for C$_{10}$H$_{14}$N$_2$O$_6$: C, 46.51; H, 5.47; N, 10.85. Found: C, 46.44; H, 5.60; N, 10.85.

cis-3,6-Bis[(acetyloxy)methyl]-5-ethoxy-3,6-dihydro-2(1H)-pyrazinone (76). To a suspension of cis-73 (0.5 g, 1.94 mmol) in methylene chloride (10 ml) under nitrogen was added 4 ml of a 1M sodium of triethyloxonium tetrafluoroborate in methylene chloride and the mixture stirred at room temperature. A second 4 ml portion of the triethyloxonium tetrafluoroborate solution was added after 6 hours. The mixture was stirred at room temperature for 24 hours and then carefully poured onto saturated aqueous sodium bicarbonate solution (30 ml). The organic layer was separated, washed with water, dried (Na$_2$SO$_4$) and concentrated under reduced pressure. The residue was recrystallized from petroleum ether affording 0.13 g (25%) of white solid mp 118°–120° C.; IR (KBr) cm$^{-1}$ 1740 (ester), 1700 (N=C), 1675 (amide); NMR (CDCl$_3$ 90 MHz) δ 1.27 (t, 3H, OCH$_2$CH$_3$), 2.05 (s, 3H, COCH$_3$), 2.12 (s, 3H, COCH$_3$), 4.03–4.50 (C, 8H, OCH$_2$CH plus OCH$_2$CH$_3$), 6.60 (s, 1H, CONH); MS (70 eV) m/e 286 (M$^+$).

cis-3,6-Bis[(t-butyldimethylsilyloxy)methyl]piperazine-2,5-dione (74). A mixture of cis-71 (1.0 g, 5.75 mmol), t-butyldimethylsilyl chloride (2.08 g, 13.8 mmol) and imidazole (1.96 g, 28.7 mmol) in dimethylformamide (15 ml) was stirred at room temperature for 10 hours. The reaction mixture was diluted with water and the solid extracted with chloroform. The organic layer was washed with water, dried (Na$_2$SO$_4$) and evaporated under reduced pressure. The solid obtained was recrystallized from ethyl acetate yielding 1.47 g (63.5%) of white crystals mp 188°–190° C.; IR (KBr) cm$^{-1}$ 1680 (amide); NMR (CDCl$_3$, 90 MHz) δ 0.11 [s, 12H, Si(CH$_3$)$_2$], 0.92 [s, 18H, Si(t-bu)], 3.7–4.17 (m, 6H, OCH$_2$CH), 6.30 (s, br, 2H, COHN). Anal. calcd. for C$_{18}$H$_{38}$N$_2$O$_4$Si$_2$: C, 53.69; H, 9.51; N, 6.96. Found: C, 53.86; H, 9.74; N, 6.91.

trans-3,6-Bis[(t-butyldimethylsilyloxy)methyl]piperazine-2,5-dione (74). A mixture of trans-71 (1.0 g, 5.75 mmol), t-butyldimethylsilyl chloride (2.08 g, 13.8 mmol) and imidazole (1.96 g, 28.7 mmol) in dimethylformamide (5 ml) was stirred at room temperature for 22 hours. The reaction mixture was diluted with water, the solid filtered and recrystallized from methanol to yield 1.47 g (63.6%) of white crystals mp 226°–228° C.; IR (KBr) cm$^{-1}$ 1680 and 1690 (amide); NMR (pyridine-$d_5$, 90 MHz) δ 0.12 [s, 12H, Si(CH$_3$)$_2$], 0.91 [s, 18H, Si(t-Bu)], 4.1–4.47 (m, 6H, OCH$_2$CH). Anal. calcd. for C$_{18}$H$_{38}$N$_2$O$_4$Si$_2$: C, 53.69; H, 9.51; N, 6.96. Found C, 53.62; H, 9.77; N, 6.98.

cis- and trans-3,6-Bis[(phenylmethoxy)methyl]-2,5-piperazinedione (75). To a suspension of O-benzyl-L-serine (12 g, 0.06 mol) in methanol (100 ml) was passed hydrogen chloride gas until the solution became clear. After refluxing for 6 hours, the solvent was concentrated under reduced pressure. The residual O-benzyl-L-serine methyl ester hydrochloride was dissolved in methanol (75 ml) and passed through a column (3×46 cm) of weak base type ion exchange resin (Amberlite IRA-45, 16–50 mesh) which had been washed with 5% aqueous sodium bicarbonate solution (500 ml) followed by water (600 ml) and methanol (400 ml). The effluent and methanol wash (500 ml) were concentrated to an oil which was kept at room temperature for 7 days. The resulting semi-solid was triturated with ethyl acetate and filtered to yield 6.17 g (56.7%) of cis- trans-75. The isomers were separated on a silica gel column by elution with chloroform. The trans isomer eluted first and was recrystallized from methanol mp 205°–207° C.; IR (KBr) cm$^{-1}$ 1675 (amide); NMR (CDCl$_3$, 300 MHz) δ 3.71 (dd, 2H, OCH$_2$CH, $J_{AB}$=9.47 Hz, $J_{AX}$=7.14 Hz), 3.80 (dd, 2H, OCH$_2$CH, $J_{AB}$=9.47 Hz, $J_{BX}$=3.34 Hz), 4.18–4.22 (m, 2H, OCH$_2$CH), 4.53 (d, 2H, OCH$_2$Ph, $J_{AB}$=11.82 Hz), 4.56 (d, 2H, OCH$_2$Ph, $J_{AB}$=11.82 Hz), 6.17 (s, 2H, CONH), 7.27–7.38 (m, 10H, Ph). Anal. calcd. for C$_{20}$H$_{22}$N$_2$O$_4$: C, 67.78; H, 6.26; N, 7.91. Found: C, 67.59; H, 6.34; N, 7.72. Continued elution with chloroform yielded the cis isomer as white crystals, mp (methanol) 173°–174° C.; IR (KBr) cm$^{-1}$ 1685 (amide); NMR (CDCl$_3$, 300 MHz) δ 3.67 (dd, 2H, OCH$_2$CH, $J_{AM}$=9.24 Hz, $J_{AX}$=8.28 Hz), 3.85 (dd, 2H, OCH$_2$CH, $J_{AM}$=9.24 Hz, $J_{MX}$=3.28 Hz), 4.18–4.22 (m, 2H, OCH$_2$CH), 4.44 (d, 2H, OCH$_2$Ph, $J_{AB}$=11.69 Hz), 4.46 (d, 2H, OCH$_2$Ph, $J_{AB}$=11.69 Hz), 6.33 (s, 2H, CONH), 7.22–7.37 (m, 10H, Ph). Anal. calcd. for $C_{20}H_{22}N_2O_4$: C, 67.78; H, 6.26; N, 7.91. Found: C, 67.58; H, 6.43; N, 7.78.

cis- and trans-2,5-Bis[(phenylmethoxy)methyl]piperazine (79). A mixture of cis- and trans-75 (0.5 g, 1.4 mmol) and lithium aluminum hydride (LAH) (0.21 g, 5.6 mmol) in dry tetrahydrofuran (THF) (50 ml) was refluxed under nitrogen for 6 hours. The mixture was cooled to room temperature and the excess LAH carefully decomposed with $Na_2SO_4.10H_2O$. The mixture was filtered, the salts extracted twice with hot THF and the combined extracts concentrated under reduced pressure yielding a semi-solid mixture of cis- and trans-79 (0.43 g) which was not further purified but used as such for the preparation of cis- and trans-80.

cis- and trans-2,5-Bis[(phenylmethoxy)methyl]-1,4-piperazine-diacetamide (80). A mixture of crude cis- and trans-79 (4.42 g, ~0.01 mol), potassium carbonate (3.74 g, 0.027 mol) and iodoacetamide (5.52 g, 0.03 mol) in absolute ethanol (50 ml) was stirred at room temperature for 24 hours. The mixture was diluted with water (50 ml) and extracted three times with chloroform (50 ml). The combined extracts were washed with water, dried ($MgSO_4$) and evaporated under reduced pressure to afford 5.19 g of crude cis- and trans-80 which were purified by chromatography (silica gel/chloroform). The trans isomer eluted first (1.17 g, 19.63%) mp (methanol) 200°–201° C.; IR (KBr) $cm^{-1}$ 1640 (amide); NMR ($CDCl_3$, 90 MHz) $\delta$ 2.41 [deceptively simple triplet (dd), 2H, axial H of ring $CH_2$], 2.57–3.60 (c, 12H, other ring H plus $NCH_2CO$ and $OCH_2$), 4.44 (s, 4H, $OCH_2Ph$), 5.43 (s, br, 2H, $CONH_2$), 7.08 (s, br, 2H, $CONH_2$), 7.31 (s, 10H, Ph). Anal. calcd. for $C_{24}H_{32}N_4O_4$: C, 65.43; H, 7.32; N, 12.72. Found: C, 65.44; H, 7.51; N, 12.57. Continued elution afforded an intermediate fraction (0.91 g, 15.27%, cis-trans mixture) followed by pure cis isomer (1.73 g, 29.02%) mp (ethyl acetate) 160°–162° C.; IR (KBr) $cm^{-1}$ 1685 (amide); NMR ($CDCl_3$, 90 MHz) $\delta$ 2.56–3.59 (c, 14H, ring H plus $NCH_2CO$ and $OCH_2$), 4.47 (s, 4H, $OCH_2Ph$), 5.54 (s, br, 2H, $CONH_2$), 7.01 (s, br, 2H, $CONH_2$), 7.31 (s, 10H, Ph). Anal. calcd. for $C_{24}H_{32}N_4O_4$: C, 65.43; H, 7.32; N, 12.72. Found: C, 65.36; H, 7.58; N, 12.68.

Pyrazine-2,5-dicarboxylic Acid (82) was prepared according to the procedure of Schut et al, supra. A mixture of 2,5-dimethylpyrazine (25 g, 0.231 mol), pyridine (500 ml), selenium (IV) oxide (125 g, 1.13 mol) and water (50 ml) was refluxed for 12–13 hours in a one liter round bottom flask equipped with a mechanical stirrer and a reflux condenser. The reaction mixture was cooled to room temperature and the precipitate A filtered and washed four times with hot pyridine-water (10:1). The combined filtrate was evaporated to dryness under reduced pressure. The residue was dissolved in 2N ammonium hydroxide solution (50 ml) and concentrated under reduced pressure. This process was once repeated and the resulting brown colored residue was dissolved in 2N ammonium hydroxide solution (180 ml) to which was added conc. hydrochloric acid solution (150 ml) to give a precipitate B. Precipitates A and B were combined and washed three times with 2N hydrogen chloride solution (70 ml) followed by ice-cold water. The solid was placed in a 2 cm diameter column and centered so that the eluate would enter a second 7 cm diameter column containing decolorising carbon Norit A (250 g, packed in water). The top column was eluted with 2N ammonium hydroxide solutionn until such time that a neutralized sample of the eluent obtained from the charcoal column showed no strong color with ferrous sulfate. To 400 ml portions of eluent (generally totalling >3 l) was added 100 ml of conc. hydrochloric acid solution to yield a white precipitate of 82. The precipitate was filtered, washed with 2N hydrochloric acid solution followed by ice-cold water and dried at approximately 75° C. under reduced pressure to yield 27.65 g (71.1%) of white solid mp 271°–272° C. (decomp.; lit. Schut, W. J., Mager, H. I. X. and Berends, W. *Rec. Trav. Chim.* 1961, 80, 391–398, mp varied between 255° and 260° C. in evacuated capillary tubes); IR (KBr) $cm^{-1}$ 1725 (carboxylic acid); NMR (20% $K_2CO_3/D_2O$, 80 MHz) 9.11 (s, ring, protons).

cis- and trans-Piperazine-2,5-dicarboxylic Acid (64). To a suspension of 82 (3.0 g, 0.02 mol) in water (90 ml) was added potassium hydroxide (3.0 g, 0.05 mol). The mixture was warmed and to the resulting solution was added Pd-C 10% (1.0 g). This mixture was hydrogenated (Parr shaker) under 40–42 psi at 50°–60° C. for 12 hours. The catalyst was filtered and the filtrate concentrated to about 30 ml under reduced pressure. Dropwise addition of conc. hydrochloric acid solution to the cooled concentrate (ice bath) afforded 1.19 g (38.5%) of white crystals mp >280° C. (trans-64) at pH 5.6–6.5 IR (KBr) $cm^{-1}$ 1635 (carboxylic acid); NMR (15% $CF_3CO_2H/D_2O$, 500 MHz) $\delta$ 3.64 [deceptively simple triplet (dd), 2H, axial H of ring $CH_2$), 4.21 (dd, 2H, equatorial H of ring $CH_2$, $J_{gem}=14.1$ Hz, $J_{ae}=3.8$ Hz), 4.53 (dd, 2H, ring CH, $J_{aa}=12.4$ Hz, $J_{ae}=3.8$ Hz). Anal. calcd. for $C_6H_{10}N_2O_4$: C, 41.38; H, 5.79; N, 16.09. Found: C, 41.32; H, 5.86; N, 16.11. Continued addition of conc. hydrochloric solution afforded 1.09 g (35.3%) of solid cis-trans mixture (pH 5.0–5.5) followed by 0.77 g (24.9%) of white crystals (cis-64) mp >280° C. (pH 4.0–5.0). IR (KBr) $cm^{-1}$ 1652 (carboxylic acid); NMR (15% $CF_3CO_2H/D_2O$, 500 MHz) $\delta$ 3.93 (dd, 2H, H of ring $CH_2$, $J_{AB}=14.5$ Ha, $J_{AX}=4.4$ Hz), 4.02 (dd, 2H, H of ring $CH_2$, $J_{AB}=14.5$ Hz, $J_{BX}=7.1$ Hz), 4.71 (q, 2H, ring CH). Anal. Calcd. for $C_6H_{10}N_2O_4$: C, 41.38; H, 5.79; N, 16.09. Found: C, 41.26; H, 5.96; N, 15.95.

trans-2,5-Dicarboxy-1,4-piperazinediacetic Acid (57). Method A, see Okaku, N., Toyoda, K., Moriguchi, Y. and Ueno, K., *Bull. Chem. Soc. Japan* 1967, 40, 2326–2332: Bromoacetic acid (5.84 g, 0.042 mol) was dissolved in water (12 ml) and the solution cooled in an ice bath. The pH was adjusted to 7–8 by dropwise addition of 6N sodium hydroxide solution. Diacid trans-64 (2.5 g, 0.014 mol) was added and the pH readjusted to 7–8. The reaction mixture was heated to 55°–65° C. and the pH raised to and maintained at 10.5–11.15. After 4 hours little or no sodium hydroxide solution needed to be added. The reaction was continued for a total of 7 hours at 55°–65° C. and then cooled to room temperature. After 10 hours, the reaction mixture was cooled (ice bath) and acidified (conc. hydrochloric acid) to pH 1–2, stored at 4° C. overnight and filtered. The solid was washed with cold water followed by acetone and dried to afford 3.11 g (76.6%) of white solid (trans-57) mp >280° C. (slow decomposition >230° C.); IR (KBr) $cm^{-1}$ 1655 (carboxylic acid); NMR (20% $K_2CO_3/D_2O$, 500 MHz) $\delta$ 2.26 [deceptively simple triplet (dd), 2H, axial H of ring $CH_2$], 2.76 (d, 2H, $NCH_2CO$, $J_{AX}=15.4$ Hz), 3.04–3.09 (m, 4H, other ring H), 3.31 (d, 2H, $NCH_2CO$, $J_{AX}=15.4$ Hz). Anal. calcd. for $C_{10}H_{14}N_2O_8.4H_2O$: C, 33.15; H, 3.87; N, 7.73. Found: C, 33.17; H, 3.85; N, 7.67.

Method B: A mixture of trans-64 (1.0 g, 5.7 mmol), bromoacetic acid (1.99 g, 14.3 mmol) and potassium carbonate (5.13 g, 37.1 mmol) in water (25 ml) was stirred at room temperature for 24 hours. The reaction mixture was cooled (ice bath) and acidified (conc. hydrochloric acid) to pH 1-2, stored at 4° C. overnight and filtered. The solid was washed with cold water followed by acetone and dried to afford 1.45 g (87.6%) of trans-57.

cis-2,5-Dicarboxy-1,4-piperazinediacetic Acid (57) was prepared from cis-64 according to conditions identical to those described under Method B for the preparation of trans-57 affording 1.09 g (66.1%) of white solid mp 200°-220° C. (slow decomp.); IR (KBr) cm$^{-1}$ 1740 and 1720 (carboxylic acid); NMR (20% $K_2CO_3/D_2O$, 500 MHz) δ 2.61 (dd, 2H, equatorial H and ring $CH_2$, J=11.3 and 3.5 Hz), 2.97 (d, 2H, $NCH_2CO$, J=15.7 Hz), 3.16-3.18 (m, 2H, ring CH), 3.23-3.25 (m, 2H, axial H of ring $CH_2$), 3.28 (d, 2H, $NCH_2CO$, J=15.8 Hz). This NMR spectrum changes with lower $K_2CO_3$ concentration. Anal. calcd. for $C_{10}H_{14}N_2O_8$: C, 41.38; H, 4.86; N, 9.65. Found: C, 41.57; H, 5.16; N, 9.56.

trans-Octahydro-1,3,7,9-tetraoxodipyrazino[1,2-a:1',2'-d]-pyrazine-2,8-(1H, 6H)-diacetamide (84). A mixture of 64 (200 mg, 1.15 mmol), potassium carbonate (396 mg, 2.8 mmol) and iodoacetamide (956 mg, 5.1 mmol) in absolute ethanol (20 ml) was refluxed for 19 hours. The reaction mixture was cooled to room temperature and the undissolved solids filtered, washed with water and dried to afford 98 mg (23.3%) of white solid mp >280° C.; IR (KBr) cm$^{-1}$ 3440 and 3300 (NH), 1740 and 1695 (imide plus amide); NMR (DMSO-$d_6$, 90 MHz) δ 2.29 [deceptively simple triplet (dd), 2H, axial H of central ring $CH_2$], 3.28-3.95 (c, 8H, other ring H), 4.19 (s, 4H, $NCH_2CO$), 7.11 (s, 2H, $CONH_2$), 7.52 (s, 2H, $CONH_2$). Anal. calcd. for $C_{14}H_{18}N_6O_6$: C, 45.90; H, 4.95; N, 22.94. Found: C, 45.72; H, 5.14; N, 22.98.

trans-1,4-Bis(2-amino-2-oxoethyl)-2,5-piperazinedicarboxylic Acid (58). A mixture of trans-64 (1.0 g, 5.7 mmol), chloroacetamide (1.28 g, 13.7 mmol) and potassium carbonate (3.48 g, 25.2 mmol) in water (25 ml) was stirred at room temperature for 35 hours. The reaction mixture was cooled (ice bath), acidified (conc. hydrochloric acid) to pH 1-2, stored at 4° C. overnight and filtered. The solid was washed with cold water followed by acetone and dried to afford 1.08 g (65.8%) of white solid mp 247°-248° C. (decomp.); IR (KBr) cm$^{-1}$ 3440 and 3310 (NH), 1705 (carboxylic acid), 1650 (amide); NMR (20% $K_2CO_3/D_2O$, 80 MHz) δ 2.39 [deceptively simple triplet (dd), 2H, axial H of ring $CH_2$], 2.86 (d, 2H, $NCH_2CO$, $J_{AB}$=16.2 Hz), 3.0-3.2 (m, 4H, other ring H), 3.36 (d, 2H, $NCH_2CO$, $J_{AB}$=16.2 Hz). Anal. calcd. for $C_{10}H_{16}N_4O_6$: C, 41.66; H, 5.59; N, 19.44. Found: C, 41.47; H, 5.44; N, 19.30.

Dimethyl trans-2,5-Bis(methoxycarbonyl)-1,4-piperazinediacetate (59). Hydrogen chloride gas was bubbled (approx. 5 min) into a stirred suspension of trans-57 (4.0 g, 13.8 mmol) in methanol (200 ml) and the mixture refluxed for 5 hours. The solvent was removed under reduced pressure and the residual solid dissolved in 10% aqueous sodium carbonate solution (50 ml) and extracted with four 50 ml portions of chloroform. The combined extract was washed with water, dried ($MgSO_4$) and the solvent removed under reduced pressure to yield 3.55 g (74.4%) of white solid (trans-59 mp (methanol) 152°-153° C.; IR (KBr) cm$^{-1}$ 1740 (ester); NMR ($CDCl_3$, 300 MHz) δ 3.07 (dd, 2H, equatorial H of ring $CH_2$, $J_{gem}$=11.3 Hz, $J_{ae}$=4.5 Hz), 3.44 (d, 2H, $NCH_2CO$, $J_{AB}$=17.1 Hz), 3.42-3.48 (m, 2H, ring H), 3.60-3.62 (m, 2H, ring H) 3.62 (d, 2H, $NCH_2CO$, $J_{AB}$=17.1 Hz), 3.69 (s, 6H, $CO_2CH_3$), 3.75 (s, 6H, $CO_2CH_3$). Anal. calcd. for $C_{14}H_{22}N_2O_8$: C, 48.55; H, 6.40; N, 8.09. Found: C, 48.87; H, 6.25; N, 8.03.

Dimethyl cis-2,5-Bis(methoxycarbonyl)-1,4-piperazinediacetate (59). Hydrogen chloride gas was bubbled through a stirred suspension of cis-57 (0.5 g, 1.72 mmol) in methanol (50 ml) until all solids dissolved. The solution was refluxed for 6 hours, the solvent removed under reduced pressure and the residual solid dissolved in 10% aqueous sodium carbonate (25 ml). The aqueous solution was extracted with four 25 ml portions of chloroform and the combined extract was washed with water, dried ($MgSO_4$) and concentrated under reduced pressure to afford 0.41 g (69.4%) of cis-59 as a viscous oil. IR (neat) cm$^{-1}$ 1745 (ester); NMR ($CDCl_3$, 300 MHz) δ 3.01 (dd, 2H, equatorial H of ring $CH_2$, $J_{AM}$=11.1 Hz, $J_{MX}$=3.6 Hz), 3.30 (dd, 2H, axial H of ring $CH_2$, $J_{AM}$=11.1 Hz, $J_{AX}$=6.6 Hz), 3.53 (s, 4H, $NCH_2CO$, 3.67-3.70 (m, 2H, other ring H), 3.70 (s, 6H, $CO_2CH_3$), 3.72 (s, 6H, $CO_2CH_3$). Anal. calcd. for $C_{14}H_{22}N_2O_8 \cdot 0.8H_2O$: C, 46.58; H, 6.10; N, 7.76. Found: C, 46.73; H, 5.84; N, 7.68.

trans-1,4-Bis(2-amino-2-oxoethyl)-2,5-piperazinedicarboxamide (61). Ammonia was condensed (5-10 ml) into a pressure bottle containing trans-59 (0.2 g, 0.58 mmol) in methanol (3 ml) held at −78° C. (acetone, dry ice). The bottle was stoppered and let stand at room temperature for 2 days. Ammonia was released slowly after cooling the bottle (ice bath). The solid was filtered, washed with methanol and dried to afford 0.14 g (85.4%) of white solid (trans-61) mp>260° C. (discoloration>230° C.); IR (KBr) cm$^{-1}$ 3420 and 3300 (NH), 1660 and 1630 (amide); NMR (15% $CF_3CO_2H/D_2O$, 80 MHz) δ 3.1-3.4 (m, 2H), 3.5-4.0 (m, 6H), 4.1-4.3 (m, 2H). Anal. calcd. for $C_{10}H_{18}N_6O_4$: C, 41.95; H, 6.34; N, 29.36. Found: C, 41.74; H, 6.43; N, 29.19.

cis-1,4-Bis(2-amino-2-oxoethyl)-2,5-piperazinedicarboxamide (61). Ammonia was passed (5-10 ml) into a pressure bottle containing cis-59 (0.5 g, 1.44 mmol) in methanol (2 ml) held at −78° C. (acetone, dry ice) and the reaction mixture worked up as in the preparation of trans-61 affording 0.38 g (92.7%) of white solid (cis-61) mp 233°-235° C. (decomp.); IR (KBr) cm$^{-1}$ 3420 and 3300 (NH), 1660 (amide); NMR (15% $CF_3CO_2H/D_2O$, 80 MHz) δ 3.35-3.90 (c, 4H, ring $CH_2$), 3.75 (s, 4H, $NCH_2CO$), 4.09-4.26 (m, 2H, ring CH). Anal. calcd. for $C_{10}H_{18}N_6O_4$: C, 41.95; H, 6.34; N, 29.36. Found: C, 41.70; H, 6.25; N, 29.09.

trans-Tetrahydro-1H,7H-pyrazino[2,1-c: 5,4-c']bis[1,4]oxazine-1,3,7,9(4H,10H)-tetrone (62). A suspension of cis-57 (0.2 g, 0.67 mmol) in acetic anhydride (2 ml) was refluxed for 1 hour. The dark reaction mixture was refluxed and the solid washed with cold water and acetone. Following drying 0.12 g (72.3%) of analytically pure off-white solid of trans-62 (slow decomposition>200° C.) was obtained. IR (KBr) cm$^{-1}$ 1820 and 1770 (anhydride); NMR (DMSO-$d_6$, 90 MHz) δ 2.61 (dd, 2H, axial H of central ring $CH_2$, J=11.0 and 8.1 Hz), 3.22 (dd, 2H, equatorial H of central ring $CH_2$, J=11.8 and 3.5 Hz), 3.62 (d, 2H, $NCH_2CO$, $J_{AB}$=17.5 Hz), 3.63 (dd, 2H ring CH, J=8.3 and 3.5 Hz), 4.02 (d, 2H, $NCH_2CO$, $J_{AB}$=17.5 Hz). Anal. calcd. for $C_{10}H_{10}N_2O_6$: C, 47.25, H, 3.97; N, 11.02. Found: C, 47.00; H, 4.02; N, 10.91.

Dimethyl Pyrazine-2,5-dicarboxylate (83). Hydrogen chloride gas was bubbled (approx. 5 min) into a stirred suspension of 82 (0.5 g, 2.97 mmol) in methanol (25 ml)

and the mixture refluxed for 4 hours. Solvent was evaporated under reduced pressure and the residual solid dissolved in chloroform. The chloroform solution was washed with 10% sodium carbonate solution and water, dried (MgSO$_4$) and evaporated under reduced pressure. Solid obtained was recrystallized from methanol to afford 0.42 g (72.2%) of colorless needles mp 167°–169° C. [lit. Spoerri, P. E. and Erickson, A. *J. Amer. Chem. Soc.* 1938, 60, 400–402, mp 168°–169° C. (sealed capillary)]; IR (KBr) cm$^{-1}$ 1720 (ester); NMR (CDCl$_3$, 90 MHz) δ 4.09 (s, 6H, CO$_2$CH$_3$), 9.40 (s, 2H, aromatic). Anal. calcd. for C$_8$H$_8$N$_2$O$_4$: C, 48.98; H, 4.11; N, 14.28. Found: C, 48.89; H, 4.33; N, 14.12.

Pyrazine-2,5-dicarboxamide (85) was prepared by the procedure of Spoerri et al., supra. Ammonia was bubbled into a refluxing solution of 83 (0.5 g, 2.55 mmol) in methanol (25 ml) for 45 minutes. The reaction mixture was cooled (ice bath), saturated with ammonia gas and allowed to stand overnight. The precipitated solid was filtered, washed with methanol and dried to afford 85 (0.41 g, 97%) mp>280° C. (Spoerri et al., supra., mp >270° C.). Anal. calcd. for C$_6$H$_6$N$_4$O$_2$: C, 43.37; H, 3.64; N, 33.73. Found: C, 43.62; H, 3.73; N, 33.50.

Dimethyl trans-Piperazine-2,5-dicarboxylate (65). A suspension of trans-64 (1.0 g, 5.7 mmol) in saturated hydrogen chloride-methanol (100 ml) was refluxed with stirring for 24 hours. The solvent was removed under reduced pressure and the residual solid dissolved in 20% sodium carbonate solution (35 ml). The solution was extracted with seven 30 ml portions of chloroform and the combined extracts washed with cold water, dried (MgSO$_4$) and evaporated under reduced pressure to yield 0.55 g (47.7%) of white solid. A small portion was recrystallized from acetone-hexane affording colorless needles mp 116°–118° C.; IR (KBr) cm$^{-1}$ 3280 and 3200 (NH), 1730 (ester); NMR (CDCl$_3$, 90 MHz) δ 2.06 (s, 2H, NH), 2.80 (dd, 2H, axial H or ring CH$_2$, $J_{gem}$=12.5 Hz, $J_{aa}$=10.0 Hz), 3.15–3.54 (m, 4H, other ring H), 3.74 (s, 6H, CO$_3$CH$_3$). Anal. calcd. for C$_8$H$_{14}$N$_2$O$_4$: C, 47.52; H, 6.98; N, 13.86. Found: C, 47.80; H, 7.03; N, 13.87.

Acidification (conc. hydrochloric acid) of the cooled (ice bath) aqueous mother liquor afforded 0.29 g of crystalline trans-64 which was recycled.

Dimethyl cis-Piperazine-2,5-dicarboxylate (65). Hydrogen chloride gas was bubbled into a stirred suspension of cis-64 (1.0 g, 5.7 mmol) in methanol (50 ml) until all solids dissolved. The solution was refluxed with stirring for 12 hours during which time it became turbid. The mixture was stirred at room temperature overnight and the solids filtered. The solids were neutralized (20% sodium carbonate solution) and extracted (chloroform) to afford 56 mg (4.87%) of white solid (trans-65) identical in all respects with the material prepared from trans-64.

The filtrate was evaporated under reduced pressure. The residual solid was dissolved in 20% sodium carbonate solution (35 ml) and extracted with six 30 ml portions of cloroform. The combined extracts were washed with cold water, dried (MgSO$_4$) and evaporated under reduced pressure to yield a colorless oil which crystallized in vacuo over several hours affording 0.79 g (69.1%) of cis-65 mp 65°–67° C.; IR (KBr) cm$^{-1}$ 3360 and 3340 (NH), 1740 and 1720 (ester); NMR (CDCl$_3$, 90 MHz) δ 2.16 (s, 2H, NH), 2.97–3.38 (m, 4H ring CH$_2$), 3.51 (q, 2H, ring CH), 3.74 (s, 6H, CO$_2$CH$_3$). Anal. calcd. for C$_8$H$_{14}$N$_2$O$_4$: C, 47.52; H, 6.98; N, 13.86. Found: C, 47.50; H, 7.04; N, 13.77.

trans-Piperazine-2,5-dicarboxamide (66). Ammonia was passed (5–10 ml) into a pressure bottle containing trans-65 (0.82 g, 4.07 mmol) in methanol (6 ml) held at −78° C. (acetone, dry ice). The bottle was stoppered and let stand at room temperature for 2 days. Ammonia was released slowly after cooling (ice bath). The solid was filtered, washed with methanol and dried to afford 0.67 g (95.4%) of white solid mp>260° C. (slow discoloration>230° C.); IR (KBr) cm$^{-1}$ 3290 and 3170 (NH), 1655 (amide); NMR (15% CF$_3$CO$_2$H/D$_2$O, 80 MHz) δ 3.60 (dd, 2H, axial H of ring CH$_2$, $J_{gem}$=13.9 Hz, $J_{aa}$=12.5 Hz), 4.15 (dd, 2H, equatorial H of ring CH$_2$, $J_{gem}$=13.9 Hz, $J_{ae}$=3.7 Hz), 4.53 (dd, 2H, ring CH, $J_{aa}$=12.5 Hz, $J_{ae}$=3.7 Hz). Anal. calcd. for C$_6$H$_{12}$N$_4$O$_2$: C, 41.85; H, 7.02; N, 32.54. Found: C, 41.69; H, 7.15; N, 32.32.

cis-Piperazine-2,5-dicarboxamide (66). Ammonia was passed (5–10 ml) into a pressure bottle containing cis-65 (0.75 g, 3.70 mmol) in methanol (5 ml) held at −78° C. (acetone, dry ice) and the reaction mixture worked up as in the preparation of trans-66 affording 0.52 g (81.5%) of white solid mp 201°–203° C. (decomp.). The filtrate was evaporated under reduced pressure and the residual solid washed with methanol and dried to yield an additional 44 mg of white solid providing a combined yield of 88.4%; IR (KBr) cm$^{-1}$ 3450 and 3300 (NH), 1695 and 1665 (amide); NMR (D$_2$O, 90 MHz) δ 2.68–3.08 (m, 4H, ring CH$_2$), 3.29 (q, 2H, ring CH), with 4.61 (s, HOD). Anal. calcd. for C$_6$H$_{12}$N$_4$O$_2$: C, 41.85; H, 7.02; N, 32.54. Found: C, 41.86; H, 7.13; N, 32.59.

Diethyl trans-2,5-Bis(carbamoyl)-1,4-piperazinediacetate (63). To a suspension of trans-66 (0.2 g, 1.16 mmol) and anhydrous potassium carbonate (0.32 g, 2.32 mmol) in 2 ml of dimethylsulfoxide (DMSO), ethyl bromoacetate (0.28 ml, 2.55 mmol) was added dropwise and the mixture stirred at room temperature for approximately 24 hours. The reaction mixture was diluted with cold water. The white solids were filtered and washed several times with cold water and once with acetone and dried affording 0.336 g (84.2%) of trans-63 mp>260° C. (slow discoloration>200° C.); IR (KBr) cm$^{-1}$ 3340 and 3200 (NH), 1730 (ester), 1665 (amide); NMR (15% CF$_3$CO$_2$H/D$_2$O, 500 MHz) δ 1.19 (t, 6H, CO$_2$CH$_2$CH$_3$), 3.38 [deceptively simple triplet (dd), 2H, axial H of ring CH$_2$], 3.67 (q, 4H, CO$_2$CH$_2$CH$_3$), 3.82–3.86 (m, 4H equatorial H of ring CH$_2$ plus NCH$_2$CO), 3.97 (d, 2H, NCH$_2$CO, $J_{AB}$=17.5 Hz), 4.28 (dd, 2H, ring CH, $J_{aa}$=10.6 Hz, $J_{ae}$=2.7 Hz). Anal. calcd. for C$_{14}$H$_{24}$N$_4$O$_6$: C, 48.83; H, 7.03; N, 16.27. Found: C, 48.79; H, 7.11; N, 16.11.

Diethyl cis-2,5-Bis(carbamoyl)-1,4-piperazinediacetate (63). To a suspension of cis-66 (0.5 g, 2.91 mmol) and anhydrous potassium carbonate (0.8 g, 5.81 mmol) in DMSO (5 ml) was added ethyl bromoacetate (0.71 ml, 6.4 mmol) dropwise. The mixture was stirred at room temperature for approximately 24 hours and filtered. The filtrate was diluted with ethyl acetate, filtered and concentrated at 50°–60° C. under reduced pressure. The resulting oily residue, which contained traces of inorganic material, was crystallized from methanol-ethyl acetate-hexane following filtration of the initially precipitated inorganic substances to afford 0.40 g (40%) of transparent crystals mp 130°–132° C.; IR (KBr) cm$^{-1}$ 3410 and 3180 (NH), 1750 and 1730 (ester), 1690 and 1665 (amide); NMR (D$_2$O, 90 MHZ) δ 1.11 (t, 6H, CO$_2$CH$_2$CH$_3$), 2.92 (d, 4H, ring CH$_2$, J=4.8 Hz), 3.29 (t, 2H, ring CH, J=4.8 Hz), 3.34 (s, 4H, NCH$_2$CO), 4.06 (q, 4H, CO$_2$CH$_2$CH$_3$), with 4.61 (s, HOD). Anal.

calcd. for $C_{14}H_{24}N_4O_6$: C, 48.83; H, 7.03; N, 16.27. Found: C, 48.81; H, 7.12; N, 16.22.

trans-Tetrahydrodipyrazino[1,2-a: 1',2'-d]pyrazine-1,3,7,9(2H,4H,8H,10H) tetrone (53). Sodium metal (31 mg, 1.35 mg atom) was added to 5 ml of absolute ethanol and stirred under nitrogen. To the solution was added diamide diester trans-63 (0.2 g, 0.58 mmol). After refluxing under nitrogen for 5 hours the solvent was removed under reduced pressure and the residual solid dissolved in cold water (5 ml) and acidified to pH 6-7 (conc. hydrochloric acid). The crystallized solid was stored at 4° C. overnight, filtered, washed with cold water followed by acetone and dried to afford 0.104 g (71.23%) of white solid mp>280° C. (slow discoloration>270° C.); IR (KBr) cm$^{-1}$ 3200 and 3100 (NH), 1730 and 1700 (imide); NMR (DMSO-d$_6$, 90 MHz) $\delta$ 2.18 [deceptively simple triplet (dd), 2H, axial H of central ring CH$_2$], 2.97-3.75 (m, 8H, other ring H), 11.22 (s, br, 2H, imide); MS (70 eV) m/e 252 (M+). Anal. calcd. for $C_{10}H_{12}N_4O_4$: C, 47.62; H, 4.80; N, 22.22. Found: C, 47.40; H, 4.81; N, 22.05.

cis-Tetrahydrodipyrazino[1,2-a : 1',2'-d]pyrazine-1,3,7,9(2H,4H,8H,10H)-tetrone (54). Sodium metal (46 mg. 2 mg atom) was added to 7 ml of absolute ethanol and stirred under nitrogen. Diamide diester cis-63 (344 mg, 1 mmol) was added to the resulting solution and the mixture refluxed under nitrogen for 6 hours. The solvent was evaporated under reduced pressure, the residual solid dissolved in cold water (5 ml) and acidified (conc. hydrochloric acid) to pH 5 (approx). The crystallized solid was stored at 4° C. overnight, filtered, washed with cold water followed by acetone and dried to afford 226 mg (89.68%) of white solid mp>260° C. (slow decomposition>200° C.); IR (KBr) cm$^{-1}$ 3250 and 3105 (NH), 1730 and 1690 (imide); NMR (DMSO-d$_6$, 90 NHz) $\delta$ 2.7-2.9 (m, br, 4H, central ring CH$_2$), 3.3-3.5 (m, 6H, other ring H), 3.55 (s, 2H, imide); MS (70 eV) m/e 252 (M+). Anal. calcd. for $C_{10}H_{12}N_4O_4$: C, 47.62; H, 4.80; N, 22.22. Found: C, 47.43; H, 4.67; N, 22.05.

trans-Tetrahydro-2,8-bis(4-morpholinylmethyl)-dipyrazino[1,2-a : 1',2'-d]-pyrazine-1,3,7,9(2H,4H,8H,10H)-tetrone (55). To a suspension of trans-53 (315 mg, 1.25 mmol) in DMSO (5 ml) was added morpholine (0.38 ml, 4.37 mmol) and formaldehyde (0.37 ml of a 37% solution, 5.0 mmol). The mixture was stirred at 55°-65° C. for 5 hours and then at room temperature overnight. DMSO was removed by distillation under reduced pressure and the residual solid triturated with ethanol, filtered, washed (ethanol) and dried to afford 488 mg (86.83%) of white solid which underwent slow decomposition above 225° C.; IR (KBr) cm$^{-1}$ 1735 and 1685 (imide); NMR (CDCl$_3$, 90 MHz) $\delta$ 2.35 [deceptively simple triplet (dd), 2H, axial H of central ring CH$_2$], 2.54-2.65 (m, 8H, NCH$_2$ of morpholine), 3.05-3.91 (c, 16H, other ring H), 4.78 (s, 4H, NCH$_2$N). Anal. calcd. for $C_{20}H_{30}O_6N_6$: C, 53.32; H, 6.71; N, 18.66. Found: C, 53.30; H, 6.76; N, 18.71.

cis-Tetrahydro-2,8-bis(4-morpholinylmethyl)-dipyrazino[1,2-a: 1',2'-d]pyrazine-1,3,7,9(2H,4H,8H,10H)-tetrone (56). To a solution of cis-54 (100 mg, 0.39 mmol) in DMSO (2 ml) was added morpholine (0.12 ml, 1.39 mmol) and formaldehyde (0.12 ml of a 37% solution, 1.59 mmol). The solution was stirred at 55°-65° C. for 5 hours and then at room temperature overnight. DMSO was removed by distillation under reduced pressure and the residual oil crystallized from ether-acetone affording 153 mg (85.95%) of white solid mp 179°-181° C. (decomp.); IR (KBr) cm$^{-1}$ 735 and 1680 (imide); NMR (CDCl$_3$, 90 MHz) 2.50-2.62 (m, 8H, NCH$_2$ of morpholine), 2.83-3.89 (c, 18H, ring H), 4.79 (s, 4H, NCH$_2$N). Anal. calcd. for $C_{20}H_{30}O_6N_6$: C, 53.32; H, 6.71; N, 18.66. Found: C, 53.10; H, 6.68; N, 18.40.

Compounds of formula 53-56 and their salts can be used as pharmaceuticals. They have antimetastatic activity and are suitable for use as an anticancer drug which is selective in destroying cancerous cells.

The compounds of the present invention have been tested for antitumor and antimetastatic activity in rats using the Lewis Lung carcinoma model. Biological evaluation of the compounds claimed herein was conducted using the Lewis Lung (LL) carcinoma model using a post-operative protocol.

The effects of the claimed compounds in the postoperative LL carcinoma model are summarized in Table 1, as shown below. The protocol included use of BDF$_1$ female mice weighing 19-21 g. LL (10$^5$ cells) was implanted IM in the leg on day 0 and the tumor bearing legs amputated on day 8. Dying mice and the mice killed on day 40 following implantation were autopsied.

Among the four compounds evaluated, the cis-bis(morpholinomethyl) analog 56 markedly inhibited the metastasis. This isomer also provided a significant increase in life span of the treated mice.

Since the parent bis(dioxopiperazine) cis-54 did not exhibit any appreciable activity in this assay, it was determined that the activity of 56 is not due to its metabolic conversion to 54. Rather, certain bis(morpholinomethyl) derivatives possess intrinsic antitumor activities, and the cis ring juncture provide the most effective morpholinomethyl derivative in the LL model.

The derivatized compounds as prepared above can be placed into any suitable dosage form for the desired end use. They can be administered to a warm-blooded animal by a variety of parenteral routes. They also can be administered orally in the form of tablets, powders, capsules, elixers and the like dosage forms. The active products can be used in admixture with common solid and liquid fillers, diluents, carriers, suspending agents and adjuvants such as, for example, cornstarch, lactose, talc, stearic acid, magnesium stearate, carboxymethyl cellulose, gelatin, acacia and locust beam gums, alcohol, water dimethylsulfoxide, vegetable oils and the like pharmaceutically acceptable materials. The liquid oral dosage form also preferably is solid reconstituted in liquid mixture at the time of administration in order to maintain stability of the dual groupings of amide and imide.

Various other examples will be apparent to the persons skilled in the art after reading the instant disclosure without departing from the spirit and scope of the invention and it is intended that all such examples are included within the scope of the following claims.

TABLE 1

Lewis Lung Carcinoma (LL) Metastasis Study[a]

| | | SURVIVAL DATA | | | | Av.Body | Av.Lung | AUTOPSY DATA[b] Av.No.of Metastasis | | |
|---|---|---|---|---|---|---|---|---|---|---|
| | Compd. | Survival Days | MST[c] | % ILS[d] | N/T[e] | Wt. (g) | Wt. (mg) | <2 mm | >2 mm | M/T[f] |
| 1. | Control | 20,23,24,25,26 28,28,28,29,32 | 27.0 | — | 0/10 | 16.3 | 741 | 0 | 49 | 10/10 |
| 2. | 53 | 18,26,28,28,31 | 28.0 | 4 | 0/5 | 16.9 | 853 | 0 | 48 | 4/4 |
| 3. | 54 | 17,19,28,29,>40 | 28.0 | 4 | 1/5 | 19.3 | 640 | 0 | 22 | 2/3 |
| 4. | 55 | 17,25,26,26,>40 | 26.0 | <0 | 1/5 | 18.9 | 700 | 0 | .38 | 3/4 |
| 5. | 56 | 19,32,>40,>40, >40 | >40 | >48 | 3/5 | 19.2 | 358 | 0 | 6 | 1/4 |

[a]BDF₁ female (19–21 g) mice; Implantation on day 0. Amputation on day 8. Post amputational schedule: 160 mg/kg from day 8, Q20 × 4 (ip). Compounds were administered in suspension (saline).
[b]Autopsy data of dying mice and mice killed day 40.
[c]Median survival time (days).
[d]Increase in life span of 25% or greater indicates activity.
[e]Number of 40 day survivors/total mice.
[f]Number of mice with metastasis/total. Mice dying of toxicity not included.

We claim:

1. A compound of the formula:

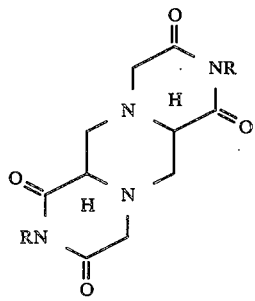

wherein R is

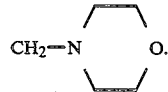

2. A pharmaceutical composition having anticancer activity which comprises, as active ingredient, the compound of claim 1, wherein R is

in association with a significant amount of a pharmaceutically acceptable carrier.

3. A pharmaceutical composition for parenteral administration and useful for the treatment of cancer which comprises, as active ingredient, the compound of claim 1, wherein R is

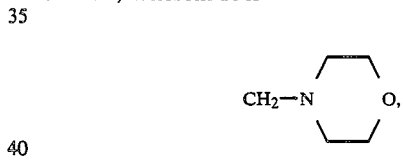

in association with a significant amount of a sterile injectable pharmaceutically acceptable carrier.

* * * * *

UNITED STATES PATENT AND TRADEMARK OFFICE
CERTIFICATE OF CORRECTION

PATENT NO. : 4,871,736
DATED : October 3, 1989
INVENTOR(S) : Raghunathan V. Nair and Donald T. Witiak It is certified that error appears in the above—identified patent and that said Letters Patent is hereby corrected as shown below:

Column 7, line 60, "exhibited cytotoxic" should be --exhibited greater cytotoxic--

Column 39, lines 25-35 (Claim 1)

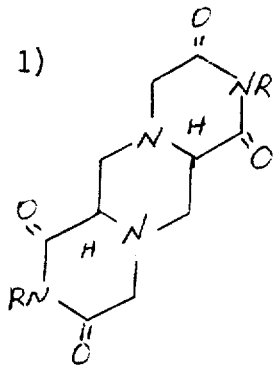

UNITED STATES PATENT AND TRADEMARK OFFICE
CERTIFICATE OF CORRECTION

PATENT NO. : 4,871,736

DATED : October 3, 1989

INVENTOR(S) : Raghunathan V. Nair and Donald T. Witiak

It is certified that error appears in the above-identified patent and that said Letters Patent is hereby corrected as shown below:

should be: 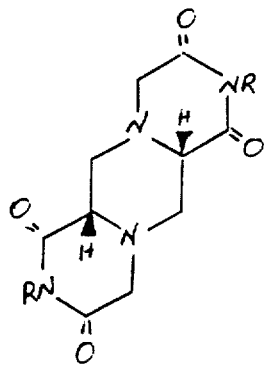

Signed and Sealed this

Eighteenth Day of December, 1990

Attest:

HARRY F. MANBECK, JR.

Attesting Officer

Commissioner of Patents and Trademarks